US011822089B2

(12) United States Patent
Yeh et al.

(10) Patent No.: US 11,822,089 B2
(45) Date of Patent: *Nov. 21, 2023

(54) HEAD WEARABLE VIRTUAL IMAGE MODULE FOR SUPERIMPOSING VIRTUAL IMAGE ON REAL-TIME IMAGE

(71) Applicant: HES IP HOLDINGS, LLC, Austin, TX (US)

(72) Inventors: Feng-Chun Yeh, Taipei (TW); Yin Chang, Taipei (TW); Guo-Hsuan Chen, Taichung (TW); Chun Hung Cho, Taipei (TW)

(73) Assignee: HES IP HOLDINGS, LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/331,910

(22) Filed: Jun. 8, 2023

(65) Prior Publication Data

US 2023/0333389 A1    Oct. 19, 2023

Related U.S. Application Data

(63) Continuation of application No. 17/623,260, filed as application No. PCT/US2021/046078 on Aug. 16, 2021, now Pat. No. 11,698,535.

(Continued)

(51) Int. Cl.
*G09G 3/00* (2006.01)
*G02B 27/01* (2006.01)
*A61B 90/00* (2016.01)

(52) U.S. Cl.
CPC .......... *G02B 27/0172* (2013.01); *A61B 90/37* (2016.02); *G09G 3/001* (2013.01);
(Continued)

(58) Field of Classification Search
CPC .............. A61B 2090/365; A61B 90/37; G02B 2027/0138; G02B 2027/014;
(Continued)

(56) References Cited

U.S. PATENT DOCUMENTS 4,953,961 A    9/1990  Ubhayakar
10,429,941 B2  10/2019 Kamoda et al.
(Continued)

FOREIGN PATENT DOCUMENTS

CN    105527710 A    4/2016
CN    106537290 A    3/2017
(Continued)

OTHER PUBLICATIONS

PCT/US2020/059317 International Search Report and Written Opinion dated Feb. 5, 2021.
(Continued)

*Primary Examiner* — Insa Sadio
(74) *Attorney, Agent, or Firm* — Chen Yoshimura LLP

(57) ABSTRACT

Disclosed are systems and methods for superimposing a virtual image on a real-time image. A system for superimposing a virtual image on a real-time image comprises a real-time image module and a virtual image module. The real-time image module comprises a magnification assembly to generate a real-time image of an object at a first location and a first depth, with a predetermined magnification. The virtual image module generates a virtual image by respectively projecting a right light signal to a viewer's right eye and a corresponding left light signal to a viewer's left eye. The right light signal and the corresponding left light signal are perceived by the viewer to display the virtual image at a second location and a second depth. The second depth is related to an angle between the right light signal and the corresponding left light signal projected to the viewer's
(Continued)

eyes. The second depth may be approximately the same as the first depth.

14 Claims, 15 Drawing Sheets

Related U.S. Application Data

(60) Provisional application No. 63/085,172, filed on Sep. 30, 2020, provisional application No. 63/065,506, filed on Aug. 14, 2020.

(52) U.S. Cl.
CPC .. *A61B 2090/365* (2016.02); *G02B 2027/014* (2013.01); *G09G 2320/0693* (2013.01); *G09G 2340/12* (2013.01); *G09G 2354/00* (2013.01); *G09G 2380/08* (2013.01)

(58) Field of Classification Search
CPC .............. G02B 26/0833; G02B 27/017; G02B 27/0172; G09G 2320/0693; G09G 2340/04; G09G 2340/12; G09G 2354/00; G09G 2380/08; G09G 3/001; G06F 3/147
See application file for complete search history.

(56) References Cited

U.S. PATENT DOCUMENTS

| | | |
|---|---|---|
| 10,467,770 B2 | 11/2019 | Sato et al. |
| 10,510,137 B1 | 12/2019 | Kitain et al. |
| 10,706,600 B1 | 7/2020 | Yoon et al. |
| 11,079,601 B2 | 8/2021 | Greenberg |
| 11,256,092 B2 | 2/2022 | Shamir et al. |
| 2002/0122217 A1 | 9/2002 | Nakajima |
| 2002/0180868 A1 | 12/2002 | Lippert et al. |
| 2004/0233275 A1 | 11/2004 | Tomita |
| 2008/0117289 A1 | 5/2008 | Schowengerdt et al. |
| 2011/0032706 A1 | 2/2011 | Mukawa |
| 2011/0273722 A1 | 11/2011 | Charny et al. |
| 2012/0002163 A1 | 1/2012 | Neal |
| 2012/0050269 A1 | 3/2012 | Awaji |
| 2012/0056799 A1 | 3/2012 | Solomon |
| 2013/0127980 A1 | 5/2013 | Haddick et al. |
| 2015/0324568 A1 | 11/2015 | Publicover et al. |
| 2015/0326570 A1 | 11/2015 | Publicover et al. |
| 2015/0338915 A1 | 11/2015 | Publicover et al. |
| 2016/0004908 A1 | 1/2016 | Lundberg |
| 2016/0062459 A1 | 3/2016 | Publicover et al. |
| 2016/0085302 A1 | 3/2016 | Publicover et al. |
| 2016/0150201 A1 | 5/2016 | Kilcher et al. |
| 2016/0238845 A1 | 8/2016 | Alexander et al. |
| 2016/0246441 A1 | 8/2016 | Westerman et al. |
| 2016/0274660 A1 | 9/2016 | Publicover et al. |
| 2016/0284129 A1 | 9/2016 | Nishizawa et al. |
| 2016/0377865 A1 | 12/2016 | Alexander et al. |
| 2017/0068091 A1* | 3/2017 | Greenberg .......... G02B 26/101 |
| 2017/0078651 A1 | 3/2017 | Russell |
| 2017/0235931 A1 | 8/2017 | Publicover et al. |
| 2017/0367651 A1 | 12/2017 | Tzvieli et al. |
| 2018/0017815 A1 | 1/2018 | Chumbley et al. |
| 2018/0091805 A1 | 3/2018 | Liang et al. |
| 2018/0157317 A1 | 6/2018 | Richter et al. |
| 2018/0182174 A1 | 6/2018 | Choi |
| 2018/0185665 A1 | 7/2018 | Osterhout et al. |
| 2018/0246336 A1 | 8/2018 | Greenberg |
| 2018/0252926 A1 | 9/2018 | Alexander et al. |
| 2018/0262758 A1* | 9/2018 | El-Ghoroury ........ H04N 13/344 |
| 2018/0292908 A1 | 10/2018 | Kamoda et al. |
| 2019/0018479 A1 | 1/2019 | Minami |
| 2019/0084419 A1 | 3/2019 | Suzuki et al. |
| 2019/0121132 A1 | 4/2019 | Shamir et al. |
| 2019/0172216 A1 | 6/2019 | Ninan et al. |
| 2019/0187473 A1 | 6/2019 | Tomizawa et al. |
| 2019/0222830 A1 | 7/2019 | Edwin et al. |
| 2019/0285897 A1 | 9/2019 | Topliss et al. |
| 2019/0293939 A1 | 9/2019 | Sluka |
| 2019/0320165 A1 | 10/2019 | French et al. |
| 2019/0361250 A1 | 11/2019 | Lanman et al. |
| 2019/0391638 A1 | 12/2019 | Khaderi et al. |
| 2020/0097065 A1 | 3/2020 | Iyer et al. |
| 2020/0117006 A1 | 4/2020 | Kollin et al. |
| 2020/0138518 A1 | 5/2020 | Lang |
| 2020/0192475 A1 | 6/2020 | Gustafsson et al. |
| 2020/0241635 A1 | 7/2020 | Cohen |
| 2020/0241650 A1 | 7/2020 | Kramer et al. |
| 2020/0249755 A1 | 8/2020 | Uscinski et al. |
| 2021/0003848 A1 | 1/2021 | Choi et al. |
| 2021/0003900 A1 | 1/2021 | Chen |
| 2021/0120222 A1 | 4/2021 | Holz et al. |
| 2021/0278671 A1 | 9/2021 | Hsiao et al. |
| 2022/0146839 A1 | 5/2022 | Miller |

FOREIGN PATENT DOCUMENTS

| | | |
|---|---|---|
| CN | 108427498 A | 8/2018 |
| CN | 109073901 A | 12/2018 |
| CN | 110168427 A | 8/2019 |
| EP | 3388921 A1 | 10/2018 |
| TW | 201716827 A | 5/2017 |
| TW | I619967 B | 4/2018 |
| WO | 2021092314 A1 | 5/2021 |
| WO | 2021258078 A1 | 12/2021 |
| WO | 2022036302 A1 | 2/2022 |

OTHER PUBLICATIONS

PCT/US2021/038318 International Search Report and Written Opinion dated Sep. 24, 2021.
PCT/US2022/015717 International Search Report and Written Opinion dated May 23, 2022.
PCT/US2022/013771 International Search Report and Written Opinion dated Apr. 14, 2022.
U.S. Appl. No. 17/179,423 Final Rejection dated Jul. 11, 2022.
U.S. Appl. No. 17/179,423 Non-Final Rejection dated Jan. 21, 2022.
Kim, J et al., "Foveated AR: Dynamically-Foveated Augmented Reality Display" pp. 1-15 [online]. Jul. 12, 2019; ACM Transactions on Graphics vol. 38, Issue 4 [Retrieved on Apr. 9, 2022]. Retrieved from the internet <url: https://dl.acm.org/doi/10.1145/3306346.3322987>; DOI: https://doi.org/10.1145/3306346.3322987.
PCT/US2021/038318 International Search Report and Written Opinion dated Jul. 28, 2022.
PCT/US2021/046078 International Preliminary Report dated Dec. 16, 2022.
PCT/US2021/046078 International Search Report and Written Opinion dated Nov. 24, 2021.
TW110132945 Non-Final Office Action dated May 26, 2023.
Taiwanese Office Action, dated Aug. 23, 2022, in a counterpart Taiwanese patent application, No. TW 109141615.
European Search Report, dated Aug. 8, 2023 in a counterpart EP patent application, No. EP21827555.0.

* cited by examiner

| Virtual binocular pixel | Pair of right pixel and left pixel | Address pointer |
|---|---|---|
| VBP(1) | RRi(1,1) & LRi(1,1) [R11 & L11] | Memory address 1 |
| VBP(2) | RRi(2,1) & LRi(1,1) [R21 & L11] | Memory address 2 |
| ... | ... | ... |
| VBP(7) | RRi(1,1) & LRi(2,1) [R11 & L21] | Memory address 7 |
| ... | ... | ... |
| VBP(37) | RRi(1,2) & LRi(1,2) [R12 & L12] | Memory address 37 |
| ... | ... | ... |
| VBP(216) | RRi(6,6) & LRi(6,6) [R66 & L66] | Memory address 216 |

FIG. 12

HEAD WEARABLE VIRTUAL IMAGE MODULE FOR SUPERIMPOSING VIRTUAL IMAGE ON REAL-TIME IMAGE

RELATED APPLICATION

This application claims the benefit of the provisional application 63/065,506, filed on Aug. 14, 2020, titled "METHODS AND SYSTEMS FOR SUPERIMPOSING REAL-TIME IMAGE WITH SUPPLEMENTARY IMAGE," and the provisional application 63/085,172, filed on Sep. 30, 2020, titled "SYSTEMS AND METHODS FOR PROJECTING VIRTUAL IMAGES WITH MULTIPLE DEPTHS", which are incorporated herein by reference at their entireties.

In addition, the PCT international application PCT/US20/59317, filed on Nov. 6, 2020, titled "SYSTEM AND METHOD FOR DISPLAYING AN OBJECT WITH DEPTHS" is incorporated herein by reference at its entirety.

BACKGROUND OF THE INVENTION

Field of the Invention

The present disclosure relates generally to methods and systems for superimposing a virtual image on a real-time image and, in particular, to methods and systems for superimposing a virtual image with depths, which is generated by projecting multiple right light signals and corresponding left lights signals to a viewer's eyes, on a real-time image.

Description of Related Art

Many visualization assistance systems and methods for aiding medical practitioners during medical exams or surgeries, including ophthalmic surgery, have been developed in recent years. During a medical procedure, the visualization assistance systems can provide additional visual information of the patients, such as medical records, operation parameters such as photograph, magnetic resonance imaging (MRI), x-ray, computed tomography (CT), or optical coherence tomography (OCT) . . . etc. In some cases, the additional visual information is a processed image of the patient, such as CT image with some marks. The visualization assistance systems are often used together with other medical instruments capable of providing real-time images of the patients. The medical practitioner may receive the additional information provided by the visualization assistance systems, separated from the real-time images. For example, the additional information is separately displayed by a monitor, instead of from a surgical microscope where the real-time image of the patent can be observed. The monitor usually can only provide a two-dimensional image. However, during medical procedures, the medical practitioner desire to observe the additional visual information (e.g. previously processed image of the patient) overlapped with the real-time image of the patient. In addition, conventional visualization assistance systems can only provide the additional visual information in a 2D image. Thus, the ability to produce three-dimensional images for additional visual information overlapped with the real-time images of the patient becomes a main interest of the medical industry. For example, in an ophthalmic exam or surgery, the medical practitioner operates by looking through the eyepieces of an ophthalmic microscope, thus viewing the real-time optical images of the patient's eye. However, the surgeon cannot observe a processed retinal image of the patient's eye at the same time through the microscope during the procedure and has to turn his/her head to observe a separate monitor and then back to the microscope. Therefore, there remains a need for incorporating additional visual information of the patient given by the visualization assistance systems with the real-time optical images viewed by the medical practitioner.

SUMMARY

An object of the present disclosure is to provide a system and a method for superimposing a virtual image on a real-time image. A system for superimposing a virtual image on a real-time image comprises a real-time image module and a virtual image module. The real-time image module comprises a magnification assembly to generate a real-time image of an object at a first location and a first depth, with a predetermined magnification.

The virtual image module generates a virtual image by respectively projecting a right light signal to a viewer's right eye and a corresponding left light signal to a viewer's left eye. The right light signal and the corresponding left light signal are perceived by the viewer to display the virtual image at a second location and a second depth. The second depth is related to an angle between the right light signal and the corresponding left light signal projected to the viewer's eyes. In one embodiment, the second depth is approximately the same as the first depth. The virtual image is superimposed on the real-time image to provide the viewer more information. Thus, in one embodiment, the virtual image is a processed image of the object.

The magnification of the real-time image is adjustable. After the real-time image is magnified, the virtual image may be manually or automatically magnified to maintain the original superimposition between the virtual image and the real-time image. An automatic mode for superimposition may be selected.

In order to superimpose the virtual image on the real-time image, the system has to be calibrated first for the viewer. Because every viewer's eyes have different physical characteristics, including interpupillary distance, the system has to be calibrated specifically for the viewer to assure that with the right light signals and left light signals projected into the viewer's eyes, the viewer would perceive the virtual image displayed at the second location and the second depth.

The process of superimposing a virtual image on a real-time image includes (a) selecting a first point on the real-time image as a first landmark, (b) displaying the real-time image at a first location and a first depth with a predetermined magnification, (c) projecting a virtual image by respectively projecting a right light signal to a viewer's right eye and a corresponding left light signal to a viewer's left eye for the viewer to perceive the virtual image at a second location and a second depth so that the corresponding first landmark on the virtual image overlaps the first landmark on the real-time image. In one embodiment, the depth of the first landmark on the real-time image is approximately the same as the depth of the corresponding first landmark on the virtual image. To have more precise superimposition, a second landmark or a third landmark may be used in a similar manner.

Additional features and advantages of the disclosure will be set forth in the descriptions that follow, and in part will be apparent from the descriptions, or may be learned by practice of the disclosure. The objectives and other advantages of the disclosure will be realized and attained by the structure and method particularly pointed out in the written description and claims thereof as well as the appended drawings. It is to be understood that both the foregoing general description and the following detailed description are exemplary and explanatory and are intended to provide further explanation of the invention as claimed.

BRIEF DESCRIPTION OF THE DRAWINGS

FIG. 12 is a table illustrating an embodiment of a look up table in accordance with the present invention.

DETAILED DESCRIPTION OF PREFERRED EMBODIMENTS

Figure 1A:
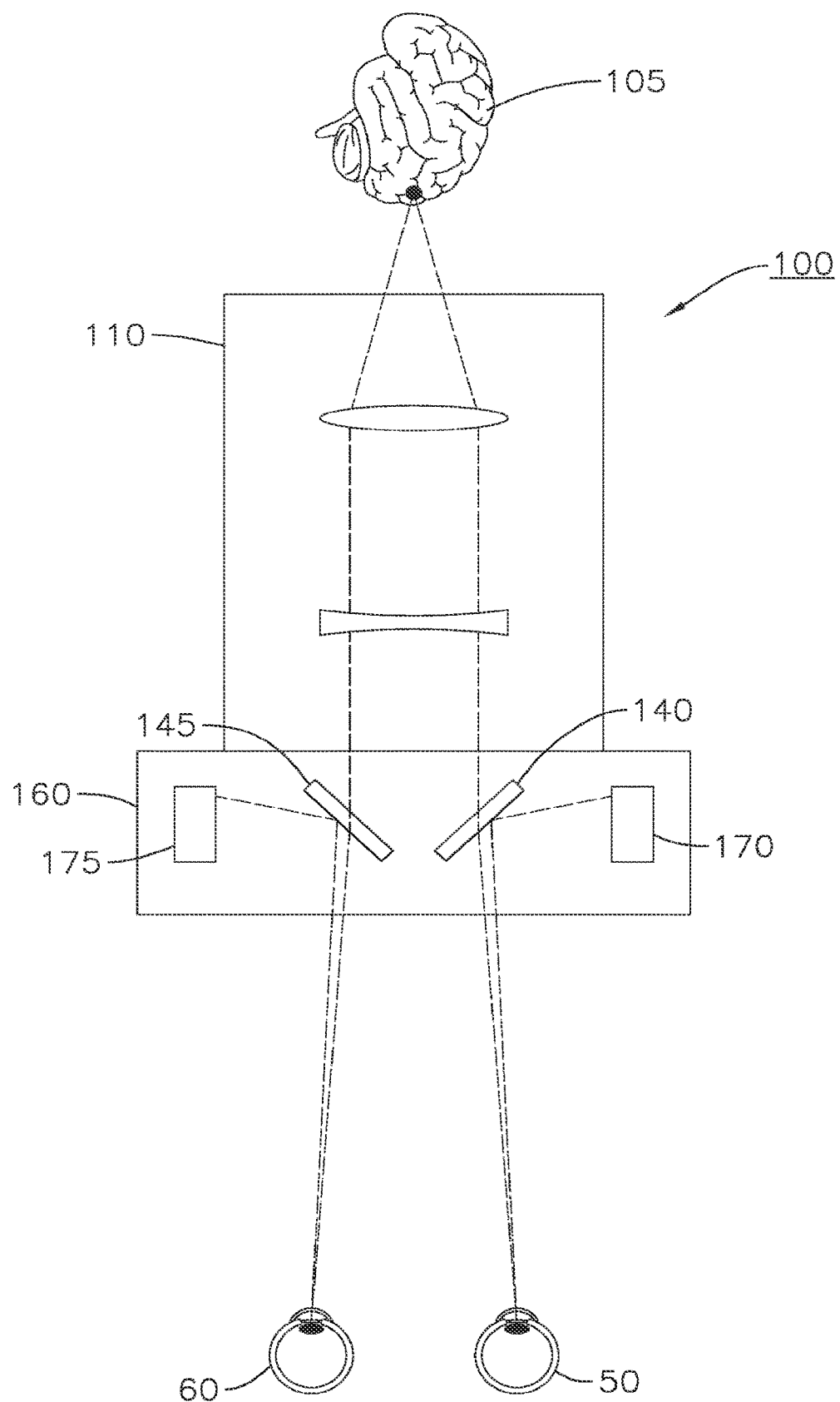
FIG. 1A is a schematic diagram illustrating an embodiment of a system in accordance with the present invention.

The terminology used in the description presented below is intended to be interpreted in its broadest reasonable manner, even though it is used in conjunction with a detailed description of certain specific embodiments of the technology. Certain terms may even be emphasized below; however, any terminology intended to be interpreted in any restricted manner will be specifically defined as such in this Detailed Description section.

The present invention relates to systems and methods for superimposing a virtual image on a real-time image. A virtual image with a depth may be superimposed on a real-time image to provide a viewer more information in connection with the real-time image, such as surgery guidance, instructions, navigation etc. The real-time image is an image that reflects changes of an object in a real-time manner. The real-time image may be a two-dimensional (2D) image or a three-dimensional (3D) image. In one embodiment, the real-time image is generated by lights reflected or emitted from the object, for example, the image observed by a microscope or a telescope. In another embodiment, the real-time image is generated by a display which receives an image of an object possibly taken by a camera in a real-time manner, for example, the image on a display from an endoscope. In addition, the real-time image may be a real image or a virtual image. The virtual image with a depth is generated by projecting light signals to the viewer's both eyes. The depth of the virtual image is related to an angle between the right light signal and the corresponding left light signal projected to the viewer's eyes. The virtual image may be a 2D image or a 3D image. When the virtual image is superimposed on the real-time image, a portion of the virtual image is overlapped with the real-time image.

A system for superimposing a virtual image on a real-time image comprises a real-time image module and a virtual image module. The real-time image module comprises a magnification assembly to generate a real-time image of an object at a first location and a first depth, with a predetermined magnification. The magnification is a process of enlarging the apparent size, not physical size, of an object. This enlargement is quantified by a calculated number also called "magnification," the ratio between the apparent (real-time image) size of an object and the observed size of the object without the magnification. The magnification is adjustable and may be any positive number such as 0.5, 1, and 10. When the magnification is less than one, it refers to a reduction in size, sometimes called minification or de-magnification.

The virtual image module generates a virtual image by respectively projecting a right light signal to a viewer's right eye and a corresponding left light signal to a viewer's left eye. The right light signal and the corresponding left light signal are perceived by the viewer to display the virtual image at a second location and a second depth. The second depth is related to an angle between the right light signal and the corresponding left light signal projected to the viewer's eyes. In one embodiment, the second depth is approximately the same as the first depth.

The virtual image is superimposed on the real-time image to provide the viewer with more information. Thus, in one embodiment, the virtual image is a processed image of the object. For example, the object may be a brain and the real-time image is the brain image generated by a surgical microscope in a real-time manner. The virtual image may be the CT or MRI image of the brain taken before the surgery and is marked with the location of brain tumor to be removed in the surgery. The marked virtual image is superimposed on the real-time image of the brain during the surgery to assist a surgeon identifying the location of the brain tumor to be removed. In this circumstance, to be accurate on the surgery location, the second depth of the virtual image (marked CT or MRI image) is approximately the same as the first depth of the real-time image, the actual brain image from a surgical microscope. The virtual image may further include some text information, marks, and pointers for guidance or explanation to assist diagnosis and treatment. In addition, the image superposition may allow the viewer to compare previous image of the object presented by the virtual image and the current status of the object presented by the real-time image and thus to estimate disease progression and treatment results.

The magnification of the real-time image is adjustable. In one embodiment, such adjustment can be achieved manually by rotating a knob, changing an objective lens, controlling a virtual switch, or giving an oral instruction. After the real-time image is magnified, the virtual image may be manually or automatically magnified to maintain the original superimposition between the virtual image and the real-time image. An automatic mode for superimposition may be selected.

In order to superimpose the virtual image on the real-time image, the system has to be calibrated first for the viewer. Because every viewer's eyes have different physical characteristics, including interpupillary distance (IPD), the system has to be calibrated specifically for the viewer to assure that with the right light signals and left light signals projected into the viewer's eyes, the viewer would perceive the virtual image displayed at the second location and the second depth. For example, the distance between the right eyepiece and the left eyepiece of a microscope need to be adjusted to fit the viewer's interpupillary distance; the angles between the right light signals and the corresponding left light signals need to be adjusted so that the virtual image is perceived by the viewer at exactly the second depth.

The process of superimposing a virtual image on a real-time image includes (a) selecting a first point of a real-time image as a first landmark, (b) displaying a real-time image at a first location and a first depth with a predetermined magnification, (c) projecting a virtual image by respectively projecting a right light signal to a viewer's right eye and a corresponding left light signal to a viewer's left eye for the viewer to perceive the virtual image at a second location and a second depth so that the corresponding first landmark on the virtual image overlaps the first landmark on the real-time image. As described above, the second depth is related to an angle between the right light signal and the corresponding left light signal projected to the viewer's eyes. In one embodiment, the depth of the first landmark on the real-time image is approximately the same as the depth of the corresponding first landmark on the virtual image. To have more precise superimposition, a second landmark or a third landmark may be used in a similar manner.

Figure 1B:
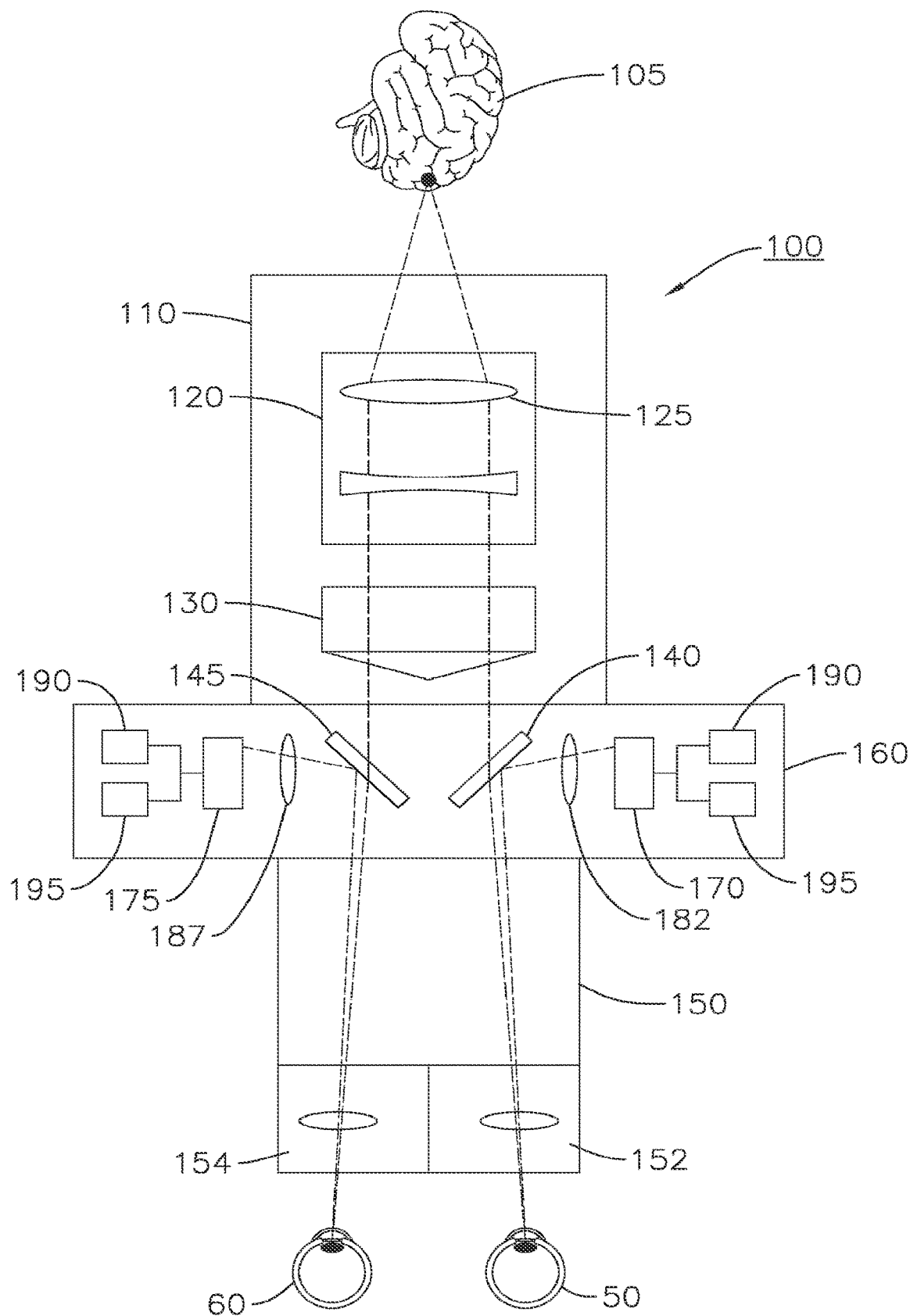
FIG. 1B is a schematic diagram illustrating another embodiment of a system in accordance with the present invention.

As shown in FIGS. 1A&1B, a system 100 for imposing a virtual image 165 on a real-time image 115 includes a real-time image module 110 and a virtual image module 160. The real-time image module 110 may include a magnification assembly 120 to generate a magnified real-time image of an object 105, such as a brain, for both eyes of a viewer. The magnification assembly 120 may include multiple optical units and assemblies, such as various types of lenses, including objective lens 113. In another embodiment, the magnification assembly 120 may use electronic circuits to process and magnify the real-time image of the object 105. The magnification of the real-time image module may be determined before observation and adjustable during the observation. The magnification may be ½, 1, 3, 10, 100, etc. The magnification adjustment may be performed via a user interface in communication with the real-time image module. The real-time image module may have one set of optical units and assemblies to generate the real-time image for both eyes of the viewer or two separate sets of optical units and assemblies to respectively generate the real-time image for the right eye and the left eye of the viewer. The real-time image module 110 may further include a prism assembly 130 to redirect the direction of lights, beam splitters 140, 145 to split the lights, an observation tube 150 to guide the lights, and eyepieces 152, 154 to further magnify the image. Again, the real-time image may be generated from the lights reflected or emitted from the object 105, such as the real-time image generated by a microscope, including a surgical microscope. In another embodiment, the real-time image may be generated by an image catching device and a display device, such as an endoscope and its associated display. Depending on the image size and resolution, the real-time image may actually or conceptually contain 921,600 pixels in a 1280×720 array. Each pixel may have a slightly different location and depth from its adjacent pixel. A representative pixel, such as a first landmark, may be selected for the real-time image. A landmark, such as the first landmark and the second landmark, is usually a unique point with a distinguishable feature that may be easily recognized by the viewer in the real-time image, such as the central point, the intersection of two specific blood vessels. A landmark may be a pixel or comprise multiple pixels adjacent to each other. In one embodiment, the location and the depth of the representative pixel may be used for those of the real-time image—the first location and the first depth.

The virtual image module 160, configured to be connected with the real-time image module 110, includes a right light signal generator 170 and a left light signal generator 175. The right light signal generator 170 generates multiple right light signals for a virtual image and is likely located closely to right portion of the real-time image module. Similarly, the left light signal generator 175 generates multiple left light signals for a virtual image and is likely located closely to left portion of the real-time image module. The right light signals are then redirected by the right beam splitter 140 towards one eye of the viewer. Similarly, the left light signals are then redirected by the left beam splitter 145 towards the other eye of the viewer. The redirected right light signals and corresponding redirected left light signals are perceived by the viewer to display the virtual image at a second depth. Depending on the image size and resolution, the virtual image may actually contain 921,600 virtual binocular pixels in a 1280×720 array. Each virtual binocular pixel may have a slightly different location and depth from its adjacent pixel. A representative virtual binocular pixel, such as a first landmark, may be selected for the virtual image. In one embodiment, the location and the depth of the representative virtual binocular pixel may be used for the virtual image—the second location and the second depth. After the viewer's eyes receiving a redirected right light signal and a corresponding redirected left light signal of the representative virtual binocular pixel, the viewer perceives the representative virtual binocular pixel at the second depth that is related to an angle between such redirected right light signal and the corresponding redirected left light signal.

The light beams of the real-time image may also pass through the right beam splitter 140 and the left beam splitter 145 towards the viewer's eyes. Thus, to certain extent, the right beam splitter 140 and the left beam splitter 145 are shared by both the real-time image module and the virtual image module. In one embodiment, the beam splitters originally installed in the real-time image module to share the real-time image with other viewers can be rotated by an appropriate angle for redirecting light signals generated from the virtual image module toward the viewer's eyes.

Figure 1C:
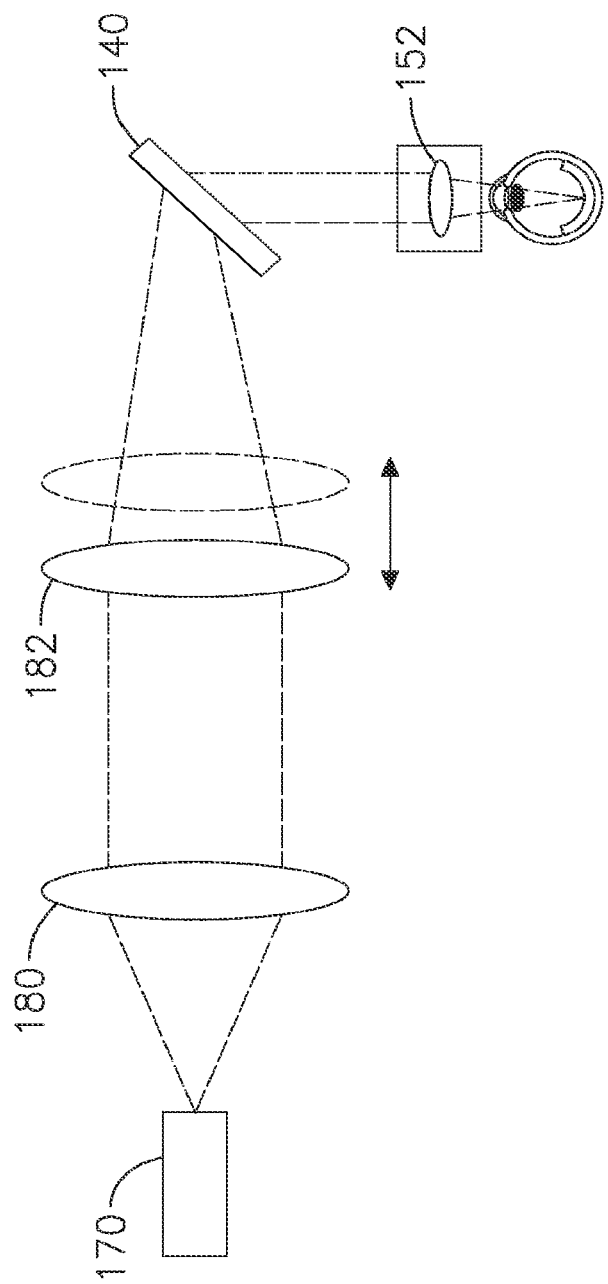
FIG. 1C is a schematic diagram illustrating a collimator in a virtual image module of a system in accordance with the present invention.

As shown in FIGS. 1B and 1C, the virtual image module 160 may further include a right focus adjustment unit 182 between the right light signal generator 170 (or the right collimator 180 if available) and right beam splitter 140 and a left focus adjustment unit 187 between the left light signal generator 175 (or the right collimator 185 if available) and the left beam splitter 145 to improve clarity of the virtual image for the viewer. The right/left focus adjustment unit may include optical units such as various types of lens, including convex lens. In one embodiment where a convex lens is used for the focus adjustment unit, adjusting its distance with the light signal generator would change the focus location of the light beams, assuming the distance between the light signal generator and the beam splitter remains the same. The closer the focus location of the light beams is to the retina, the clear the virtual image is for the viewer. Since the axial length of viewers' eyes may vary, the preferred focus location of light beams and, thus, the distance between the light signal generator and the focus adjustment unit vary accordingly. In other words, for the viewer with longer axial length, the focus adjustment unit needs to be more far away from the light signal generator so that the focus location of the light beams is closer to the viewer's retina. When the collimator is available, the focus adjustment unit is positioned between the collimator and the beam splitter. After passing through the collimator, the light beams from the light signal generator become substantially parallel and then converge after passing through the focus adjustment unit. In addition, since the focus adjustment unit does not alter the incident angle of light beams, the depth of the virtual image would be unaffected.

As partly shown in FIG. 1C, the virtual image module 160 may further include a right collimator 180 and a left collimator 185 to narrow the light beam of the multiple light signals, for example to cause the directions of motion to become more aligned in a specific direction or to cause spatial cross section of the light beam to become smaller. The right collimator 180 may be positioned between the right light signal generator 170 and the right beam splitter 140 and the left collimator 185 may be positioned between the left light signal generator 175 and the left beam splitter 145. The collimator may be a curved mirror or lens.

In addition, the virtual image module 160 may include a control module 190 to control virtual image signals for the right light signal generator 175 and the left light signal generator 175. The control module 190 is communicatively connected to the virtual image module 160 to adjust the right light signals and the corresponding left light signals so that the virtual image may be automatically modified to superimpose the virtual image on the real-time image based on a variation of the real-time image. The variation of the real-time image includes the variation in view angle, magnification, or location. For example, when the magnification of the real-time image is adjusted such as from 3 times to 10 times, the control module 190 would process the image signals to magnify the virtual image to the same size and use at least the first landmark to cause the virtual image to continue being superimposed on the real-time image. Although the control module 190 includes one or more processors, for complicated signal processing, the control module 190 may use an external server 250 for calculations.

The virtual image may be stored in a memory module 195. In one embodiment, the virtual image is a processed image of the object, such as an X-ray image, an ultrasound image, a CT image, and a MRI image of the object with some marks or highlights on the area of interest. The virtual image may further include some text information and pointers for guidance or explanation. For example, the virtual image may be a previously taken and processed retinal image of a patient with marks on bleeding blood vessels to be sealed by laser. The system 100 may superimpose such a virtual image on the real-time image of the same retina from a slit-lamp microscope. The control module 190 may retrieve the virtual image stored in the memory module 195 and then generate virtual image signals for the right light signal generator 170 and the left light signal generator 175 whenever necessary.

Figure 2:
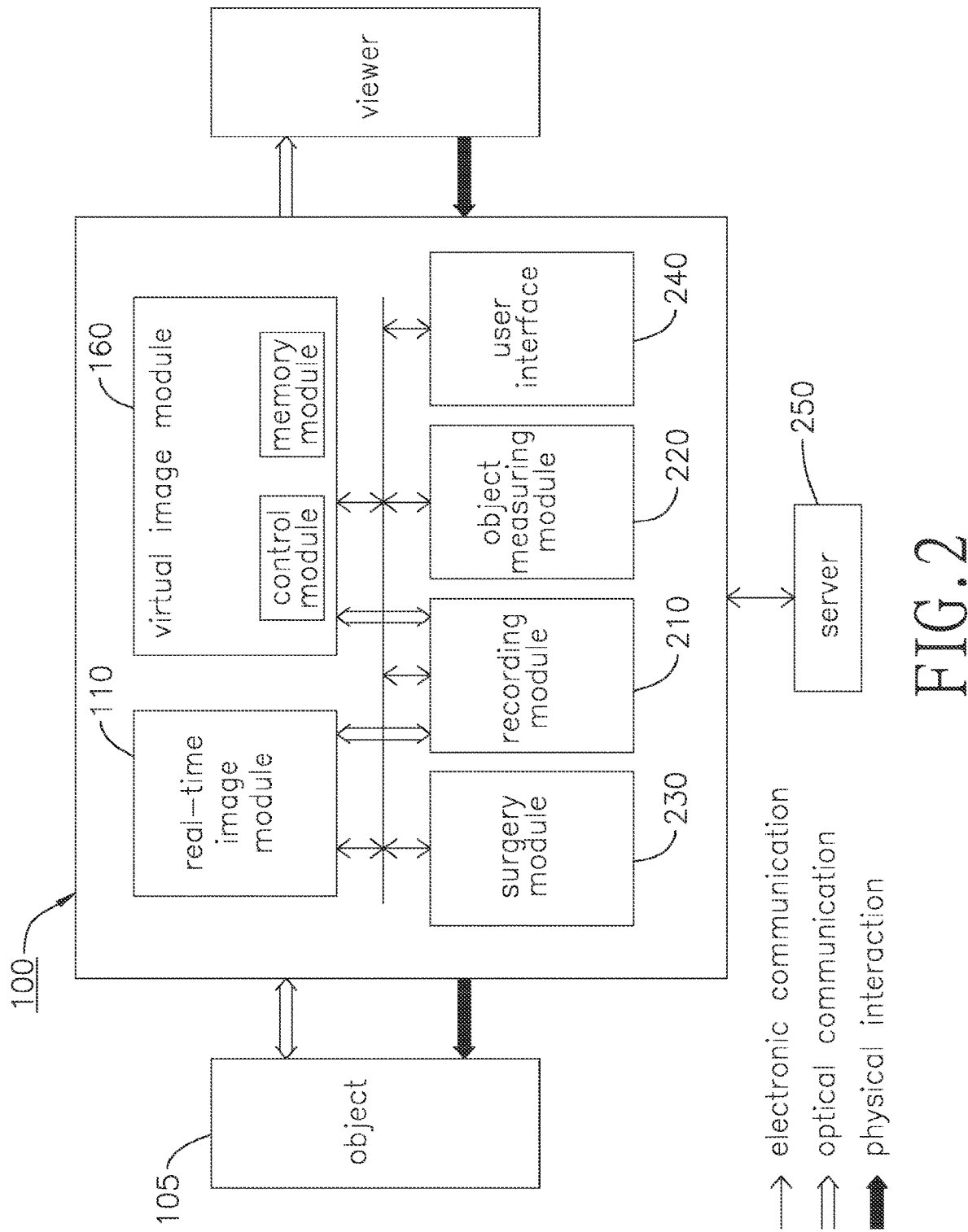
FIG. 2 is a block diagram illustrating an embodiment of a system with various modules in accordance with the present invention.

As shown in FIG. 2, in addition to the real-time image module 110 and the virtual image module 160, the system 100 may further include a recording module 210 to record either or both the real-time image and the virtual image, an object measuring module 220 to measure a location and a depth of the object, a surgery module 230 to physically perform a surgery on the object 105, and a user interface 240 for the viewer to communicate with various modules of the system 100 and to control various functions of the system 100. All modules of the system 100 may have electronic communication with each other via wired or wireless manner. The wireless manner may include WiFi, bluetooth, near field communication (NFC), internet, telecommunication, radio frequency (RF), etc. The real-time image module 110, the virtual image module 160, and the recording module 210 may have optical communication with each other via optical beams and optical signals. The viewer may observe the real-time image and the virtual image through the system 100 and then control the system 100 via physical interaction with the user interface 240. The system 100 may have optical communication with the object 105 such as receiving light beams reflected or emitted from the object, and projecting light beams on the object. The system 100 may have physical interactions with the object 105, such as performing a laser surgery on the object.

As described above, the system 100 may further include a recording module 210 to record either or both of the real-time image and the virtual image. In one embodiment, the recording module 210 may be positioned between the right beam splitter 140 and the left beam splitter 145 to record the real-time image—the light beams from the object and respectively reflected by the right beam splitter and the left beam splitter during a surgery. The recording module 210 may include a digital camera or a charge-coupled device (CCD) to capture the image. In another embodiment, the recording module 210 may be positioned adjacent to the eyepieces to record the light beams passing through the eyepieces but before arriving the viewer's eyes, including both light beams forming the real-time image and the virtual image. The recording module 210 may be connected to the control unit to directly record the virtual image signals and the associated information and parameters for future displaying.

As described above, the system 100 may further include an object measuring module 220 to measure a location and a depth of the object. The object measuring module 220 configured to be connected to the system may continuously or periodically measure the location and depth of the object relative to the object measuring module (or the viewer), and communicate the associated information to the virtual image module for adjusting the virtual image. Upon receipt of such information, the control module 190 may process the virtual image signals based on the updated location and depth of the object relative to the object measuring module and the viewer. As a result, the virtual image may remain superimposed on the real-time image. The distance or relative location between the object 105 and the object measuring module 220 (or the viewer's eyes) may change along the time. In one situation, the object 105, such as a portion of human body like eyeballs, may move during a surgery. In another situation, the system 100 may be worn by a viewer, such as a surgeon, and the viewer may move his/her head during a surgery. Thus, the relative location and distance between the object 105 and the viewer's eye need to be measured and calculated in order to maintain the superimposition of the virtual image on the real-time image. The object measuring module 220 may include a gyroscope, indoor/outdoor global positioning system (GPS) and a distance measurement components (e.g. emitters and sensors) to precisely track the variation of such relative location and depth of the object 105.

As described above, the system 100 may further include a surgery module 230 to physically perform a surgery on the object 105. The surgery module 230 may include a laser to remove tissues or to seal bleeding blood vessels, and/or a scalpel to cut tissues. The surgery module 230 may coordinate with the real-time image module 110 to position the laser and/or the scalpel towards the spot of interest identified by the viewer, e.g. a surgeon, as shown in the real-time image.

As described above, the system 100 may further include a user interface 240 for the viewer to control various functions of the system 100, for example the magnification of the real-time image, the second location and the second depth of the virtual image, the focus adjustment unit, the recording module 210, the object measuring module 220, etc. The user interface 240 may be operated by voices, hand gestures, finger/foot movements and in the form of a pedal, a keyboard, a mouse, a knob, a switch, a stylus, a button, a stick, a touch screen, etc. The user interface 240 may communicate with other modules (including the real-time image module 110, the virtual module 160, the recording module 210, the object measuring module 220, and the surgery module 230) of the system 100 via wired or wireless manner. The wireless manner may include WiFi, bluetooth, near field communication (NFC), internet, telecommunication, radio frequency (RF), etc. The viewer may use the user interface 240, such as controlling a stick, to move a cursor to a spot of interest on the real-time image, and then use the user interface 240, such as pressing a pedal, to initiate the laser beam towards the corresponding spot of interest on the object 105 for removing the tissue or sealing a bleeding blood vessel.

Figure 3A:
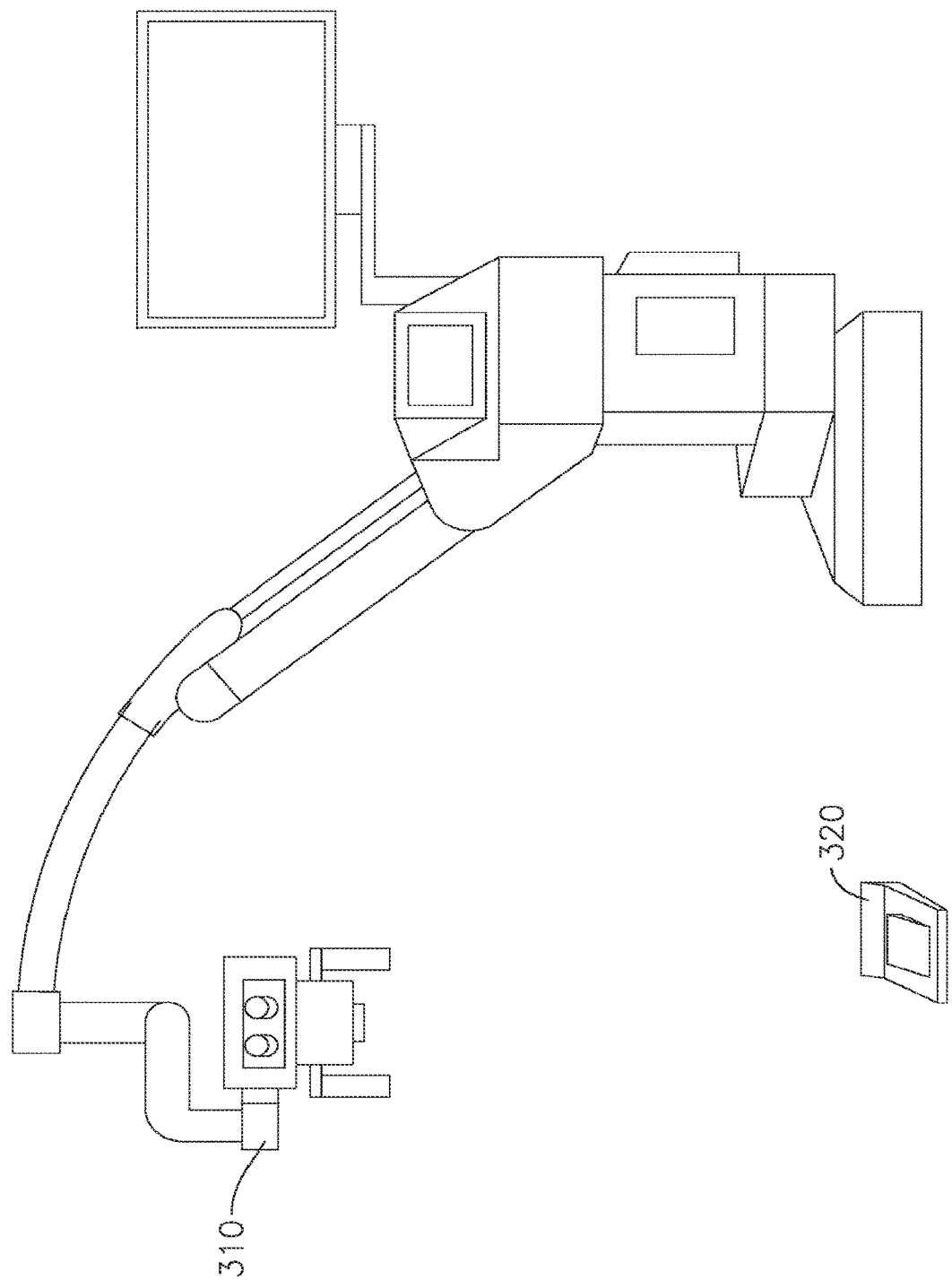
FIGS. 3A and 3B are schematic diagrams illustrating possible embodiments of a system in accordance with the present invention.
Figure 3B:
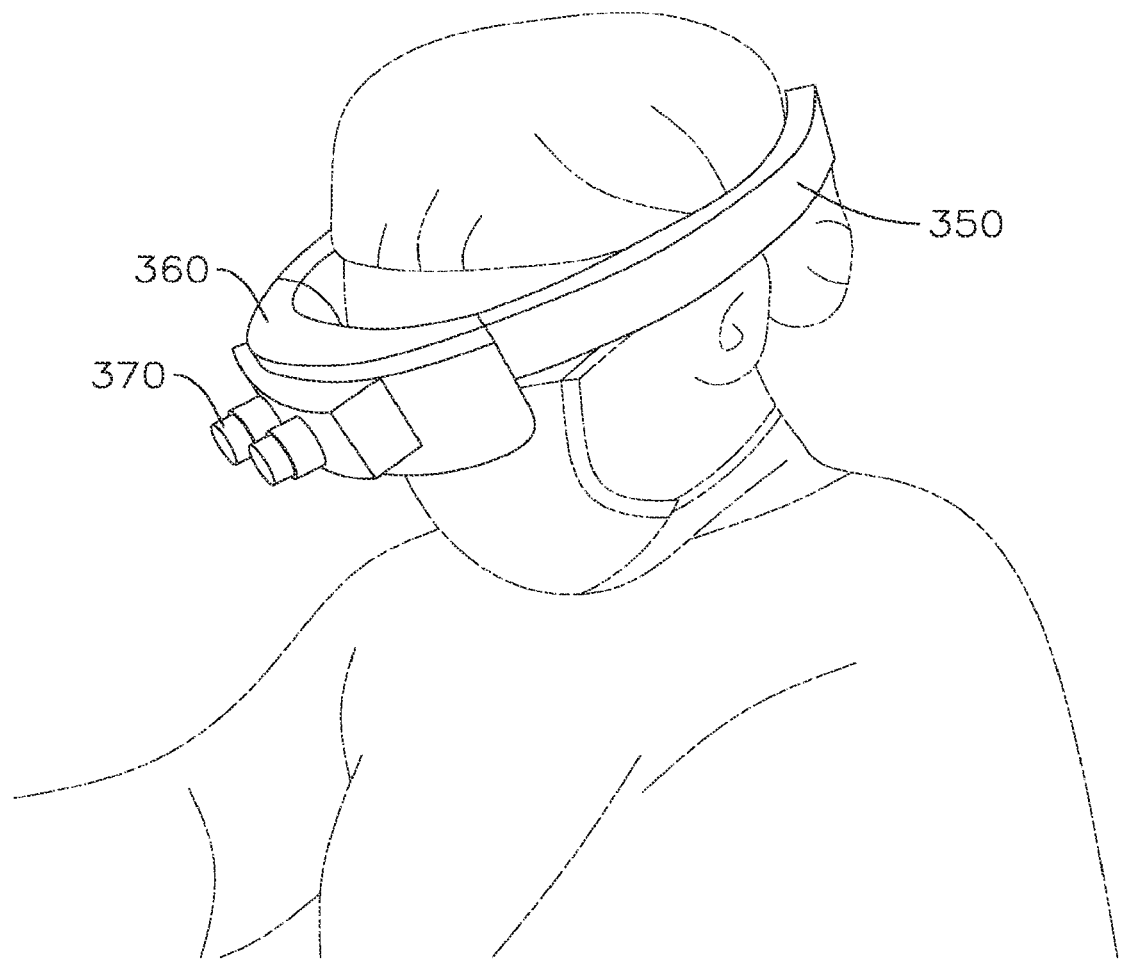

In one embodiment, the system 100 may be an AR microscope for surgery and/or diagnosis, such as an AR ophthalmoscope and an AR slit-lamp microscope. FIG. 3A shows an example of a stationary AR surgical microscope 310 which includes a user interface pedal 320. FIG. 3B shows an example of a portable AR surgical microscope 350, a head wearable device, which includes a real-time image module 370 and a virtual image module 360. The real-time image module 370 is attached to but separable from the virtual image module 360.

Figure 4:
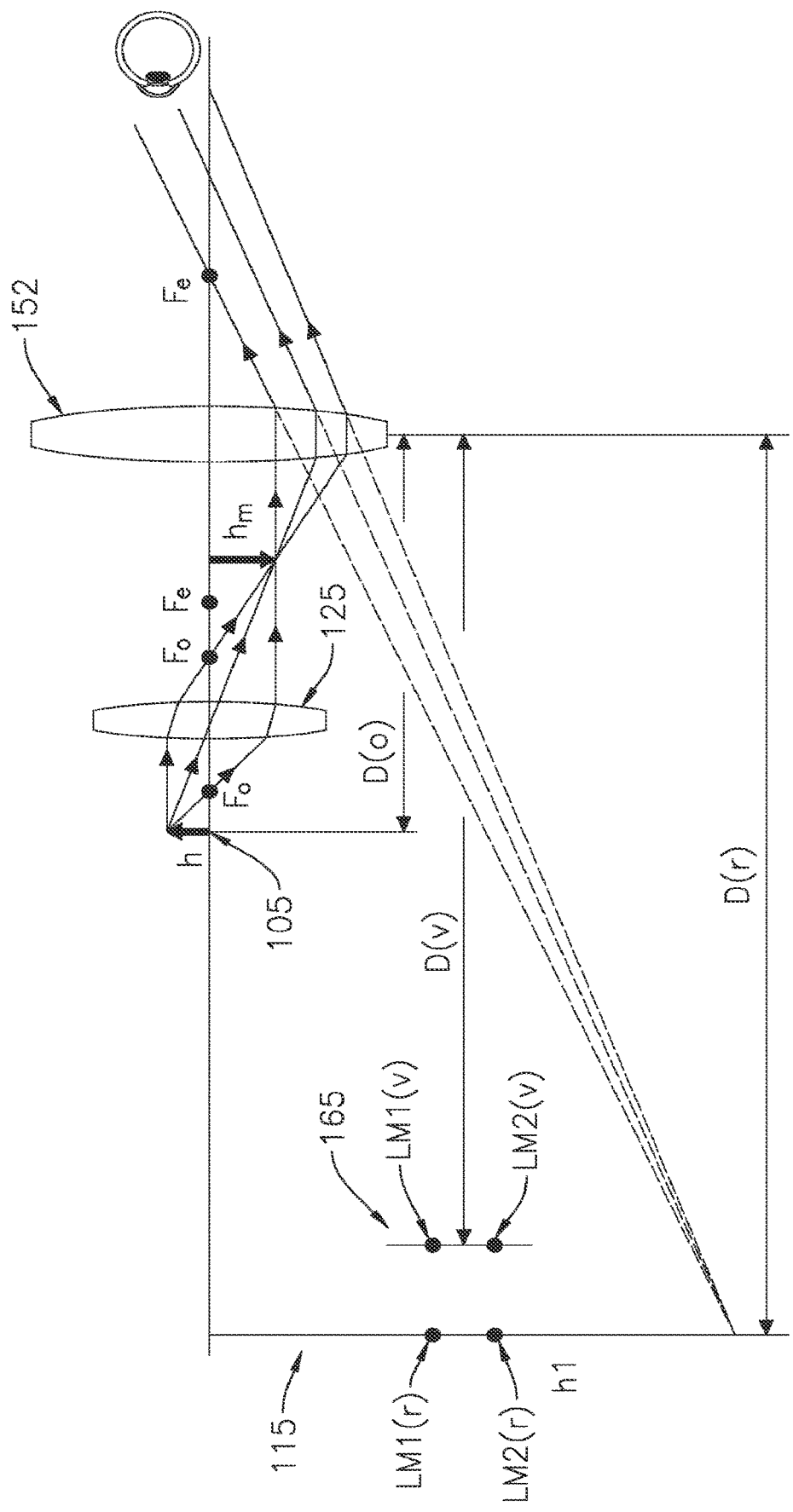
FIG. 4 is a schematic diagram illustrating an embodiment of the relationship between an object, a real-time image, and a virtual image in accordance with the present invention.

As shown in FIG. 4, the object 105, the real-time image 115 generated by the real-time image module 110, and the virtual image 165 generated by the virtual image module 160, may have different locations and depths. In this embodiment, the virtual image 165 is a processed partial image of the object 105. The virtual image module 160 may only generate the virtual image 165 for the field or area of interest of the object. The image of the object may be captured and processed, for example by an artificial intelligence (AI) module, for generating the virtual image within a very short time interval such as a second.

As described before, depending on the resolution, the object 105, the real-time image 115, and the virtual image 165 may conceptually or actually comprise a large number of pixels, such as 921,600 pixels in a 1280×720 array. In this embodiment, the location and the depth of the object 105, the real-time image 115, and the virtual image 165 are respectively represented by the location and depth of their corresponding first landmark. A depth is measured based on the distance between the eyepiece 152 and either the object 105, or the real-time image 115, or the virtual image 165. Accordingly, as shown in FIG. 4, the object 105 is located at the object location L(o) and object depth D(o); the real-time image 115, a magnified image of the object 105, is located at the first location L(r) and the first depth D(r); and the virtual image 165 is located at the second location L(v) and the second depth D(v). Depending on the optical features of the real-time image module, the depth of the real-time image 115 may be closer or farther to the viewer's eyes. In this embodiment, the depth of the real-time image D(r) is greater than the depth of the object D(o). However, the depth of the real-time image D(r) may be less than or about the same as the depth of the object D(o) in other embodiments. Then the virtual image 165 is generated by the virtual image module 160 at the depth D(v) which is closer to the eyepiece than the real-time image 115.

With the information of L(r) and D(r), as shown in FIG. 4, the virtual image module 160 of the system 100 may superimpose the virtual image on the real-time image by overlapping the corresponding first landmark LM1(v) on the virtual image with the first landmark LM1(r) on the real-time image. For a higher level of superimposition, the virtual image module 160 of the system 100 may further overlap the corresponding second landmark LM2(v) on the virtual image with the second landmark LM2(r) on the real-time image. In another embodiment where the superimposition goes beyond overlapping the landmarks with respect to their locations, the depth of the corresponding first landmark on the virtual image may be approximately the same as the depth of the first landmark on the real-time image. Similarly, the depth of the corresponding second landmark on the virtual image may be approximately the same as the depth of the second landmark on the real-time image. To precisely and completely superimpose a 3D virtual image on a 3D real-time image, in addition to the first landmark and the second landmark, the third landmark on the real-time image is selected. Then the virtual image module causes the location and the depth of the corresponding third landmark on the virtual image to be approximately the same as those of the third landmark on the real-time image.

Figure 5:
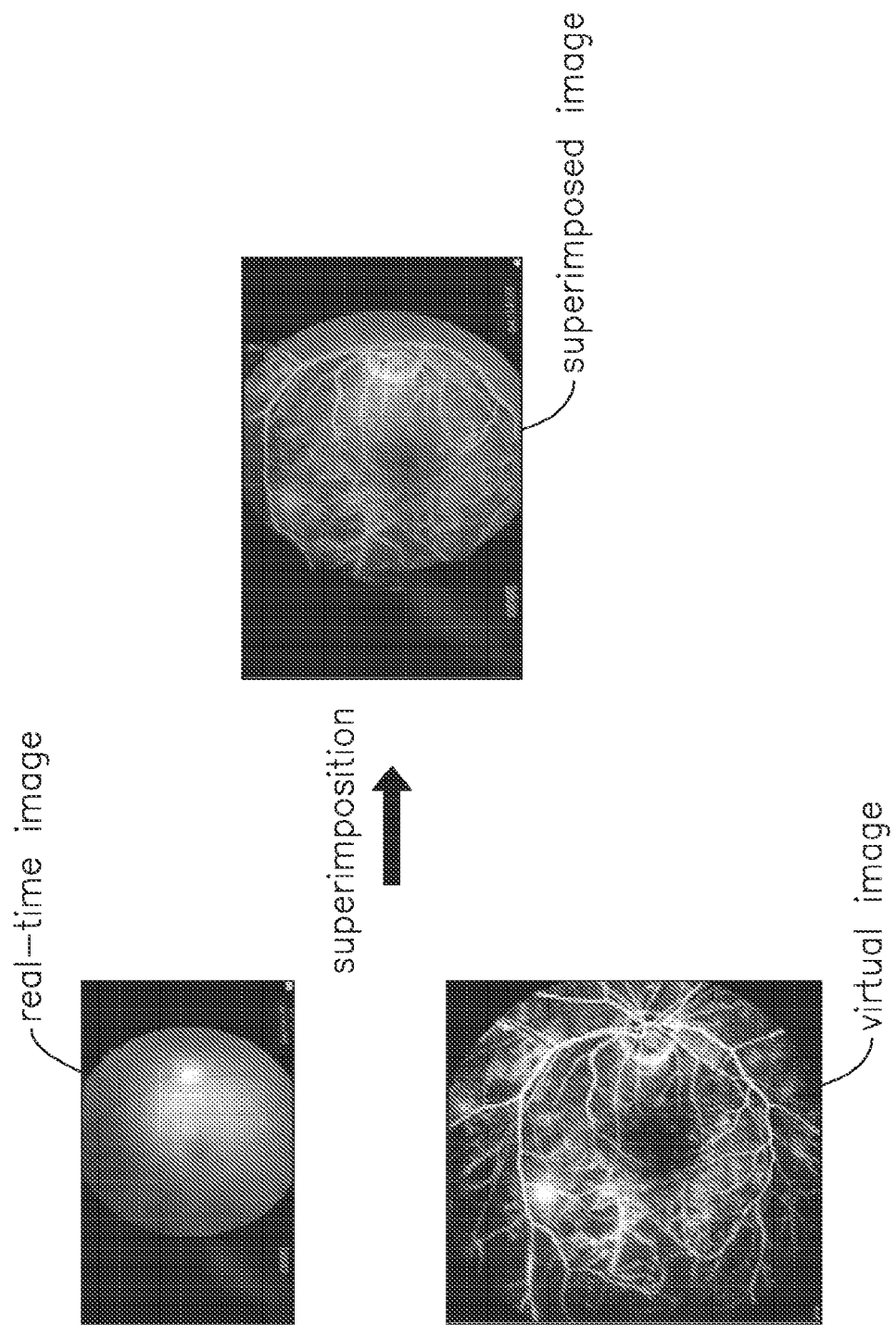
FIG. 5 are photos illustrating superimposition of a virtual image of a retina on a real-time image in accordance with the present invention.

FIG. 5 demonstrates three images—a real-time image of a patient's retina, a processed virtual image of the retina, and the superimposed image of both. In one embodiment, the angiographic image of the patent's retina is captured possibly by a slit-lamp biomicroscope and processed. Then the virtual image module 160 may use such processed image to project a virtual image superimposed on the real-time image of the patent's retina during a surgery to help identify and visualize the edges of choroidal neovascular membrane. The AR/MR microscope may greatly facilitate the diagnosis and treatment of various ophthalmic disorders and diseases.

Figure 6:
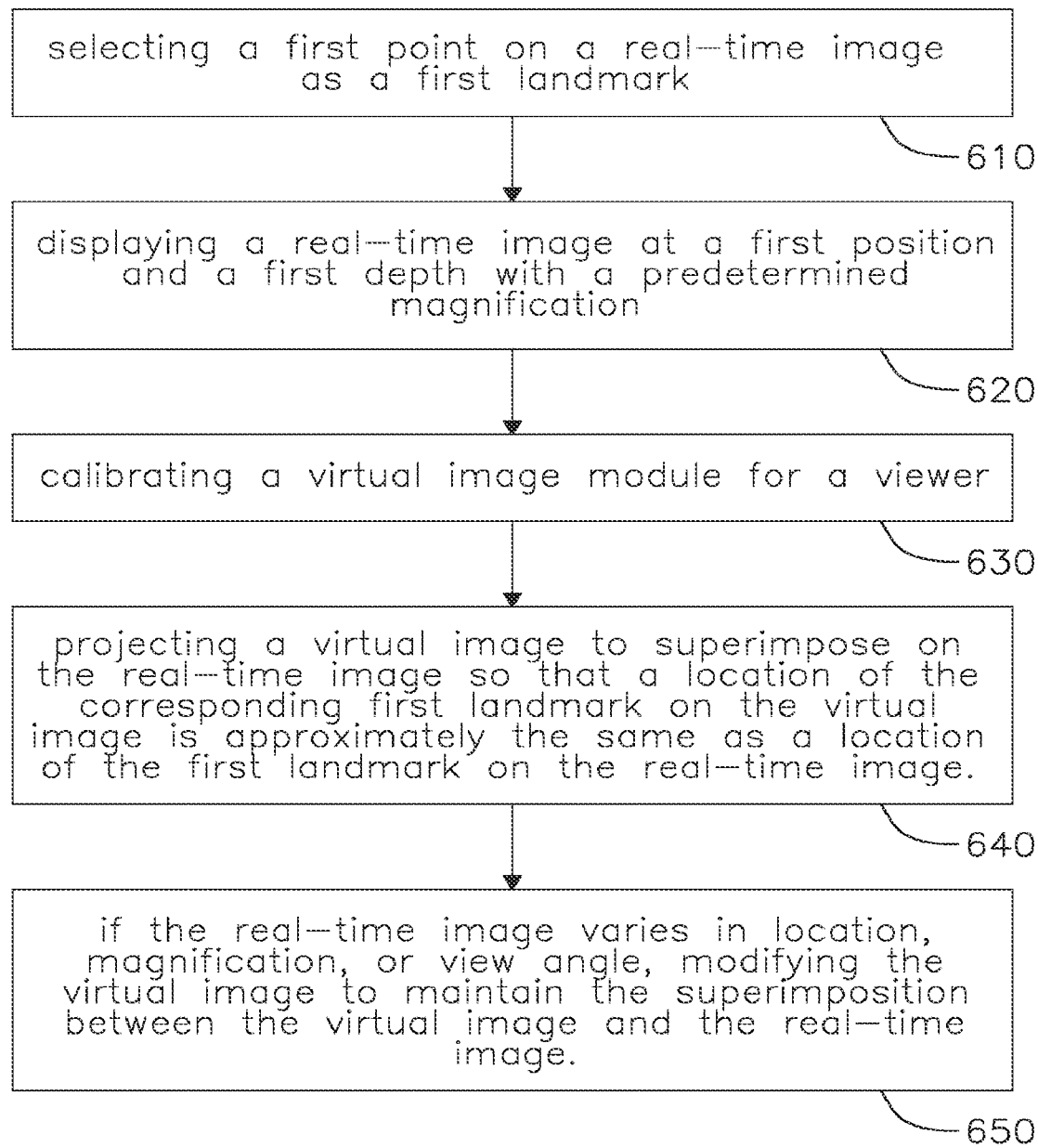
FIG. 6 is a flow chart illustrating an embodiment of processes for superimposing a virtual image on a real-time image in accordance with the present invention.

As shown in FIG. 6, the process of superimposing a virtual image on a real-time image includes 4 steps. At step 610, a first point on a real-time image is selected as a first landmark by a viewer, an expert, a computer, or the system 100. For example, a viewer may control a mouse or stick to move a cursor or pointer viewable from the eyepieces to select the first landmark on the real-time image. As described above, a landmark, including a first landmark, a second landmark, and a third landmark, is usually a unique point with a distinguishable feature that may be easily recognized by the viewer in the real-time image, such as the central point, the intersection of two specific blood vessels. Landmarks may be defined either manually by experts or automatically by a computer program. There are three basic types of landmarks: anatomical landmarks, mathematical landmarks and pseudo-landmarks. An anatomical landmark is a biologically-meaningful point in an organism. Any anatomic feature—a fold, prominence, duct, vessel, etc.— consistently present in a tissue that serves to indicate a specific structure or position. Anatomic landmarks may be used by surgical pathologists for specimen orientation. Mathematical landmarks are points in a shape that are located according to some mathematical or geometrical property, for instance, a high curvature point or an extreme point. A computer program may determine mathematical landmarks used for an automatic pattern recognition. Pseudo-landmarks are constructed points located between anatomical or mathematical landmarks. A typical example is an equally spaced set of points between two anatomical landmarks to get more sample points from a shape. Pseudo-landmarks are useful during shape matching, when the matching process requires a large number of points. A landmark may be a pixel or comprise multiple pixels adjacent to each other.

At step 620, a real-time image of the object is displayed at a first location and a first depth with a predetermined magnification. As described above, there are at least two types of real-time image. The first type of real-time image is generated by lights reflected or emitted from the object, for example, the image observed by a microscope or a telescope. In this situation, the first location and the first depth may be determined by the optical features of the real-time image module. The viewer may observe the real-time image through the eyepieces. The second type of real-time image is generated by a display which receives an image of an object possibly taken by a camera in a real-time manner, for example, the image on a display from an endoscope, including gastroscope, colonoscope or proctoscope. The endoscope may have two image capturing devices positioned separately to take and generate a 3D image. The real-time image may be a two-dimensional (2D) image or a three-dimensional (3D) image. Step 610 and step 620 are exchangeable.

At step 630, the virtual image module is calibrated for a specific viewer. As described before, some physical characteristic of each viewer, such as interpupillary distance, may affect the location and depth of the virtual image the viewer perceives with the same right light signals and the corresponding left light signals. In one embodiment, the control module may adjust the virtual image signals based on the viewer's IPD so that the right light signal generator 170 and the left light signal generator 175 can project the light signals at appropriate locations and angles to assure the viewer perceives the virtual image at exactly the second location and the second depth.

At step 640, the virtual image module projects a virtual image by respectively projecting a right light signal to a viewer's right eye and a corresponding left light signal to a viewer's left eye for the viewer to perceive the virtual image at a second location and a second depth so that the corresponding first landmark on the virtual image overlaps the first landmark on the real-time image. In other words, the virtual image module projects a virtual image to superimpose on the real-time image. At least the location of the corresponding first landmark on the virtual image (second location) is approximately the same as the location of the first landmark on the real-time image (first location). In general, the virtual image is divided into multiple virtual binocular pixels, depending on the resolution, for example 921,600 virtual binocular pixels in a 1280×720 array. For each right light signal and its corresponding left light signal projected onto the viewer's retinas, the viewer perceives a virtual binocular pixel at a specific location and depth. The depth is related to the angle of the right light signal and the corresponding left light signal projected into the viewer's eye. When the first landmark on the real-time image is at the first location and the first depth, the virtual binocular pixel of the corresponding first landmark on the virtual image is projected to be perceived by the viewer at the second location and the second depth. For an initial superimposition, the location of the corresponding first landmark on the virtual image (second location) is set to be approximately the same as the location of the first landmark on the real-time image (first location) while their depths may be different. This superimposition can be achieved manually by the viewer or automatically by the system 100 using shape recognition technologies, including artificial intelligence (AI) algorithms. To further improve the superimposition, the second depth is set to be approximately the same as the first depth. In addition, if the real-time image is magnified from the actual size of the object, the virtual image needs to be magnified to the same extent for superimposition. Moreover, to further improve the superimposition, the view angle of the virtual image needs to match the view angle of the real-time image. The relationship between the light signals generated by the light signal generators and the depth perceived by the viewer is described in details below.

At step 650, if the real-time image varies in location, magnification, or view angle, the virtual image module modifies the virtual image to maintain the superimposition between the virtual image and the real-time image. The variation of the location, magnification, and view angle of the real-time image may be caused by the viewer's operation or by the movement of the object or the viewer. The system 100 constantly monitors the first location and first depth of the real-time image and the second location and the second depth of the virtual image. Once any variation of the real-time image occurs, the virtual image module modifies the virtual image signal to maintain the superimposition between the virtual image and the real-time image.

Figure 7:
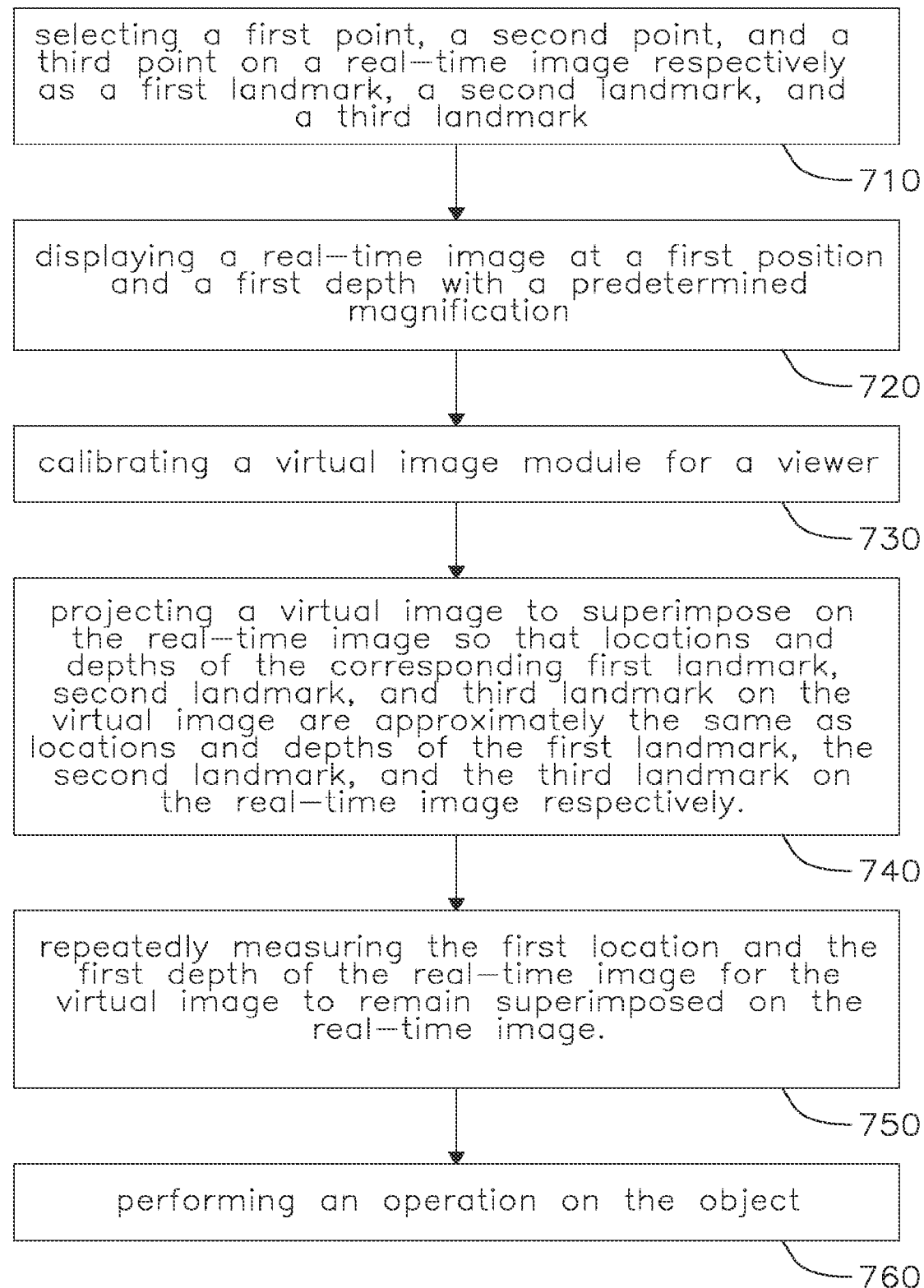
FIG. 7 is a flow chart illustrating another embodiment of processes for superimposing a virtual image on a real-time image in accordance with the present invention.

As shown in FIG. 7, an alternate process of superimposing a virtual image on a real-time image includes 6 steps. Some steps are the same or similar to those described in the prior embodiment shown in FIG. 6. Some steps are optional and can be further altered. At step 710, a first point, a second point, and a third point on a real-time image are respectively selected as a first landmark, a second landmark, and a third landmark by a viewer, an expert, a computer, or the system 100. For the most precise superimposition, three landmarks are used here. Some surgeries, such as brain neurosurgery, requires very high level of accuracy, and thus three landmarks may be required to assure the virtual image is completely superimposed on the real-time image. However, depending on the needs, the process may include two landmarks. Step 720 may be the same as step 620 and step 730 may be the same as step 630. Step 740 follows the same principles described for step 640. However, the locations and depths of the corresponding first landmark, second landmark, and third landmark on the virtual image are approximately the same as the locations and the depths of the first landmark, the second landmark, and the third landmark on the real-time image respectively. At step 750, the first location and the first depth are repeatedly monitored or measured. The first location and the first depth may be calculated based on the location and depth of the object relative to the object measuring module (or the viewer) measured by the object measuring module. As a result, the virtual image is able to remain superimposed on the real-time image. At step 760, the viewer, e.g. a surgeon, performs an operation on the object by a laser or a scalpel at the spot of interest identified by the viewer.

Figure 8:
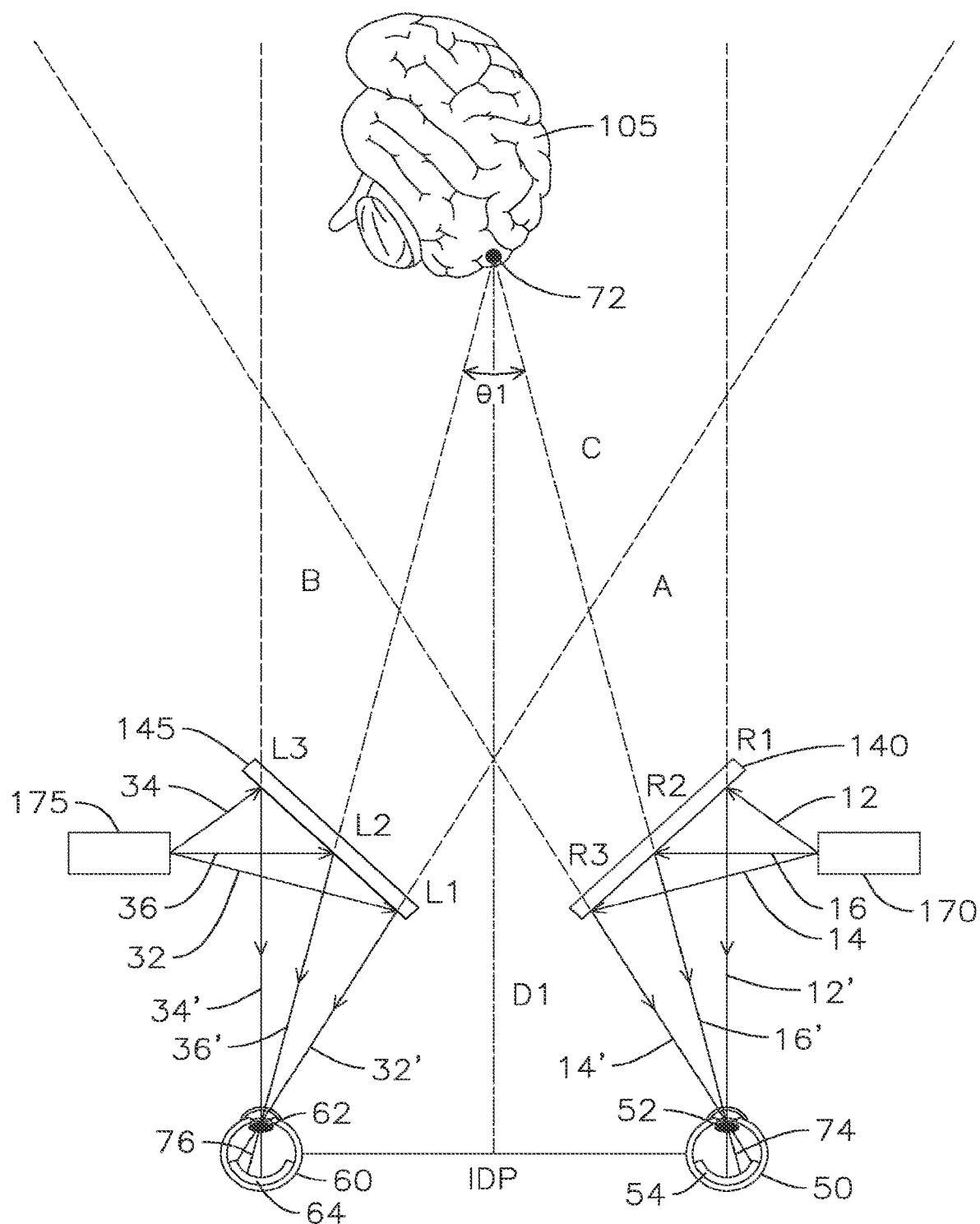
FIG. 8 is a schematic diagram illustrating an embodiment of a virtual image module in accordance with the present invention.

The virtual image module 160 and the method of generating a virtual image 165 at a second location and a second depth as well as the method of moving the virtual image as desired are discussed in details below. The PCT international application PCT/US20/59317, filed on Nov. 6, 2020, titled "SYSTEM AND METHOD FOR DISPLAYING AN OBJECT WITH DEPTHS" is incorporated herein by reference at its entirety. As shown in FIG. 8, the virtual image module 160 includes a right light signal generator 170 to generate multiple right light signals such as 12 for RLS_1, 14 for RLS_1 and 16 for RLS_3, a right beam splitter 140 to receive and redirect the multiple right light signals towards the right retina 54 of a viewer, a left light signal generator 175 to generate multiple left light signals such as 32 for LLS_1, 34 for LLS_2, and 36 for LLS_3, and a left beam splitter 145 to receive and redirect the multiple left light signals towards a left retina 64 of the viewer. The viewer has a right eye 50 containing a right pupil 52 and a right retina 54, and a left eye 60 containing a left pupil 62 and a left retina 64. The diameter of a human's pupil generally may range from 2 to 8 mm in part depending on the environmental lights. The normal pupil size in adults varies from 2 to 4 mm in diameter in bright light and from 4 to 8 mm in dark. The multiple right light signals are redirected by the right beam splitter 140, pass the right pupil 52, and are eventually received by the right retina 54. The right light signal RLS_1 is the light signal farthest to the right the viewer's right eye can see on a specific horizontal plan. The right light signal RLS_2 is the light signal farthest to the left the viewer's right eye can see on the same horizontal plane. Upon receipt of the redirected right light signals, the viewer would perceive multiple right pixels for the object 105 in the area A bounded by the extensions of the redirected right light signals RLS_1 and RLS_2. The area A is referred to as the field of view (FOV) for the right eye 50. Likewise, the multiple left light signals are redirected by the left beam splitter 145, pass the center of the left pupil 62, and are eventually received by the left retina 64. The left light signal LLS_1 is the light signal farthest to the right the viewer's left eye can see on the specific horizontal plan. The left light signal LLS_2 is the light signal farthest to the left the viewer's left eye can see on the same horizontal plane. Upon receipt of the redirected left light signals, the viewer would perceive multiple left pixels for the object 105 in the area B bounded by the extensions of the redirected left light signals LLS_1 and LLS_2. The area B is referred to as the field of view (FOV) for the left eye 60. When both multiple right pixels and left pixels are displayed in the area C which are overlapped by area A and area B, at least one right light signal displaying one right pixel and a corresponding left light signal displaying one left pixel are fused to display a virtual binocular pixel with a specific depth in the area C. The depth is related to an angle of the redirected right light signal and the redirected left light signal projected into the viewer's retinas. Such angle is also referred to as a convergence angle.

Figure 9:
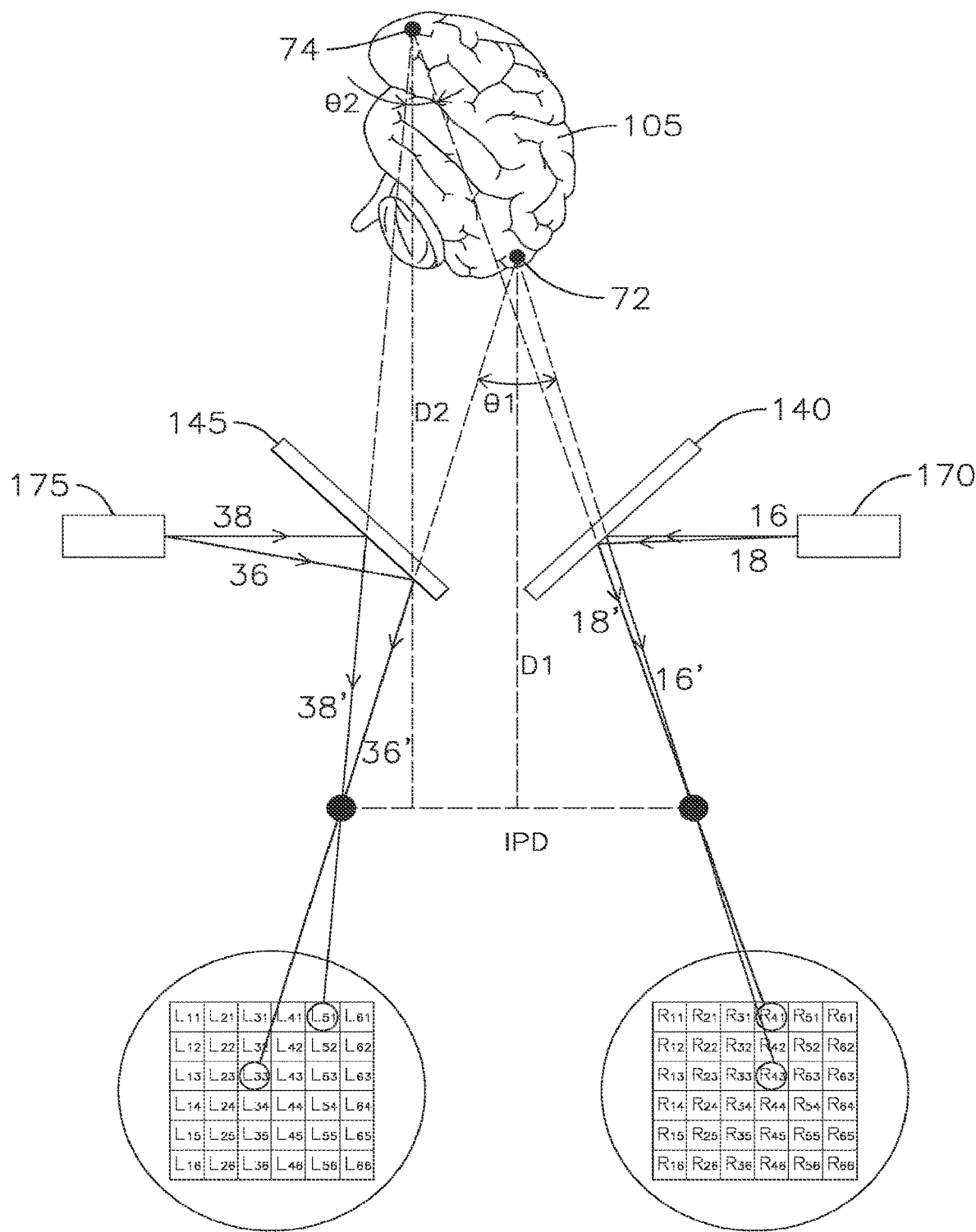
FIG. 9 is a schematic diagram illustrating a relationship between a virtual binocular pixel and the corresponding pair of the right pixel and left pixel in accordance with the present invention.

As shown in FIGS. 8 and 9, the viewer perceives a virtual image of the brain object 105 with multiple depths in the area C in front of the viewer. The image of the brain object 105 includes a first virtual binocular pixel 72 displayed at a first depth D1 and a second virtual binocular pixel 74 displayed at a second depth D2. The first angle between the first redirected right light signal 16' and the corresponding first redirected left light signal 26' is θ1. The first depth D1 is related to the first angle θ1. In particular, the first depth of the first virtual binocular pixel of the object 105 can be determined by the first angle θ1 between the light path extensions of the first redirected right light signal and the corresponding first redirected left light signal. As a result, the first depth D1 of the first virtual binocular pixel 72 can be calculated approximately by the following formula:

$$\operatorname{Tan}\left(\frac{\theta}{2}\right) = \frac{IPD}{2D}$$

The distance between the right pupil 52 and the left pupil 62 is interpupillary distance (IPD). Similarly, the second angle between the second redirected right light signal 18' and the corresponding second redirected left light signal 38' is θ2. The second depth D2 is related to the second angle θ2. In particular, the second depth D2 of the second virtual binocular pixel of the object 105 can be determined approximately by the second angle θ2 between the light path extensions of the second redirected right light signal and the corresponding second redirected left light signal by the same formula. Since the second virtual binocular pixel 74 is perceived by the viewer to be further away from the viewer (i.e. with larger depth) than the first virtual binocular pixel 72, the second angle θ2 is smaller than the first angle θ1.

Furthermore, although the redirected right light signal 16' for RLG_2 and the corresponding redirected left light signal 36' for LLS_2 together display a first virtual binocular pixel 72 with the first depth D1. The redirected right light signal 16' for RLG_2 may have the same or different view angle from the corresponding redirected left light signal 36' for LLS_2. In other words, although the first angle θ1 determines the depth of the first virtual binocular pixel, the redirected right light signal 16' for RLG_2 may be or may not be a parallax of the corresponding redirected left light signal 36' for LLS_2. Thus, the intensity of red, blue, and green (RB G) color and/or the brightness of the right light signal and the left light signal may be approximately the same or slightly different because of the shades, view angle, etc. to better present some 3D effects.

As described above, the multiple right light signals are generated by the right light signal generator, redirected by the right beam splitter, and then directly scanned onto the right retina to form a right retina image on the right retina. Likewise, the multiple left light signals are generated by left light signal generator, redirected by the left beam splitter, and then scanned onto the left retina to form a left retina image on the left retina. In an embodiment shown in FIG. 9, a right retina image 80 contains 36 right pixels in a 6×6 array and a left retina image 90 also contains 36 left pixels in a 6×6 array. In another embodiment, a right retina image 80 contains 921,600 right pixels in a 1280×720 array and a left retina image 90 also contains 921,600 left pixels in a 1280×720 array. The virtual image module 160 is configured to generate multiple right light signals and corresponding multiple left light signals which respectively form the right retina image on the right retina and left retina image on the left retina. As a result, the viewer perceives a virtual image with specific depths in the area C because of image fusion.

With reference to FIG. 9, the first right light signal 16 from the right light signal generator 170 is received and reflected by the right beam splitter 140. The first redirected right light signal 16', through the right pupil 52, arrives the right retina of the viewer to display the right pixel R43. The corresponding left light signal 36 from the left light signal generator 175 is received and reflected by the left beam splitter 145. The first redirected light signal 36', through the left pupil 62, arrives the left retina of the viewer to display the left retina pixel L33. As a result of image fusion, a viewer perceives the virtual image with multiple depths where the depths are determined by the angles of the multiple redirected right light signals and the corresponding multiple redirected left light signals. The angle between a redirected right light signal and a corresponding left light signal is determined by the relative horizontal distance of the right pixel and the left pixel. Thus, the depth of a virtual binocular pixel is inversely correlated to the relative horizontal distance between the right pixel and the corresponding left pixel forming the virtual binocular pixel. In other words, the deeper a virtual binocular pixel is perceived by the viewer, the smaller the relative horizontal distance at X axis between the right pixel and left pixel forming such a virtual binocular pixel is. For example, as shown in FIG. 9, the second virtual binocular pixel 74 is perceived by the viewer to have a larger depth (i.e. further away from the viewer) than the first virtual binocular pixel 72. Thus, the horizontal distance between the second right pixel and the second left pixel is smaller than the horizontal distance between the first right pixel and the first left pixel on the retina images. Specifically, the horizontal distance between the second right pixel R41 and the second left pixel L51 forming the second virtual binocular pixel is four-pixel long. However, the distance between the first right pixel R43 and the first left pixel L33 forming the first virtual binocular pixel is six-pixel long.

Figure 10:
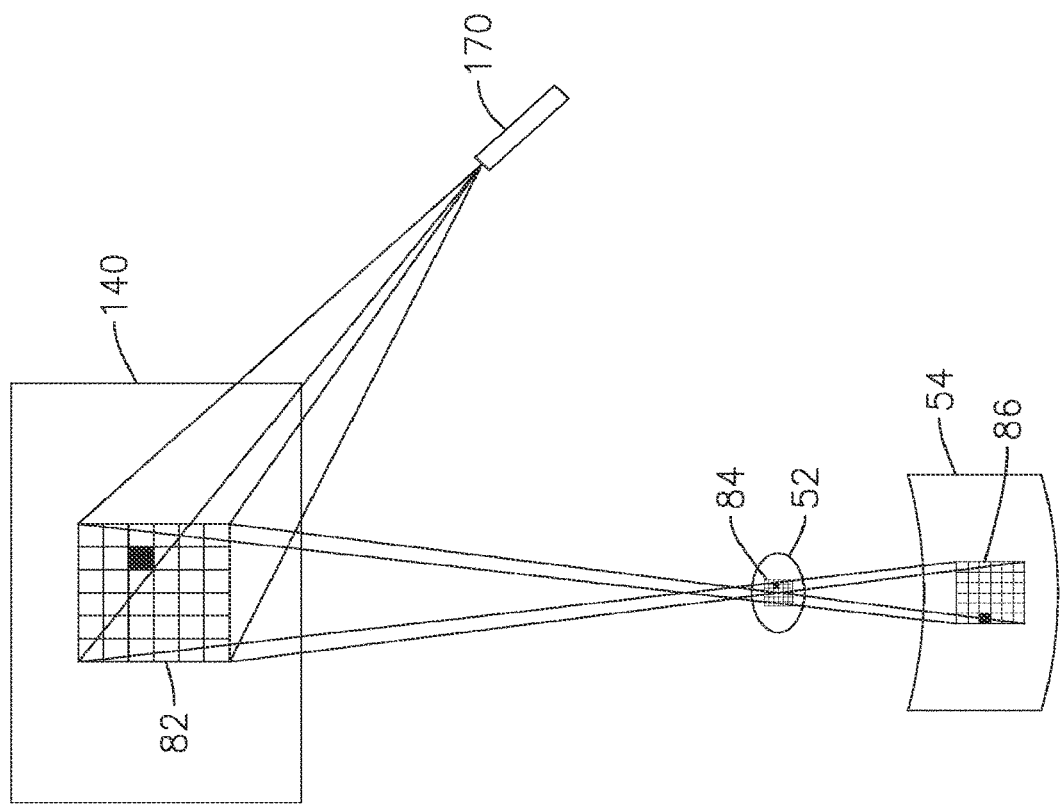
FIG. 10 is a schematic diagram illustrating the light path from a light signal generator to a beam splitter, and to a retina of a viewer in accordance with the present invention.
Figure 10:
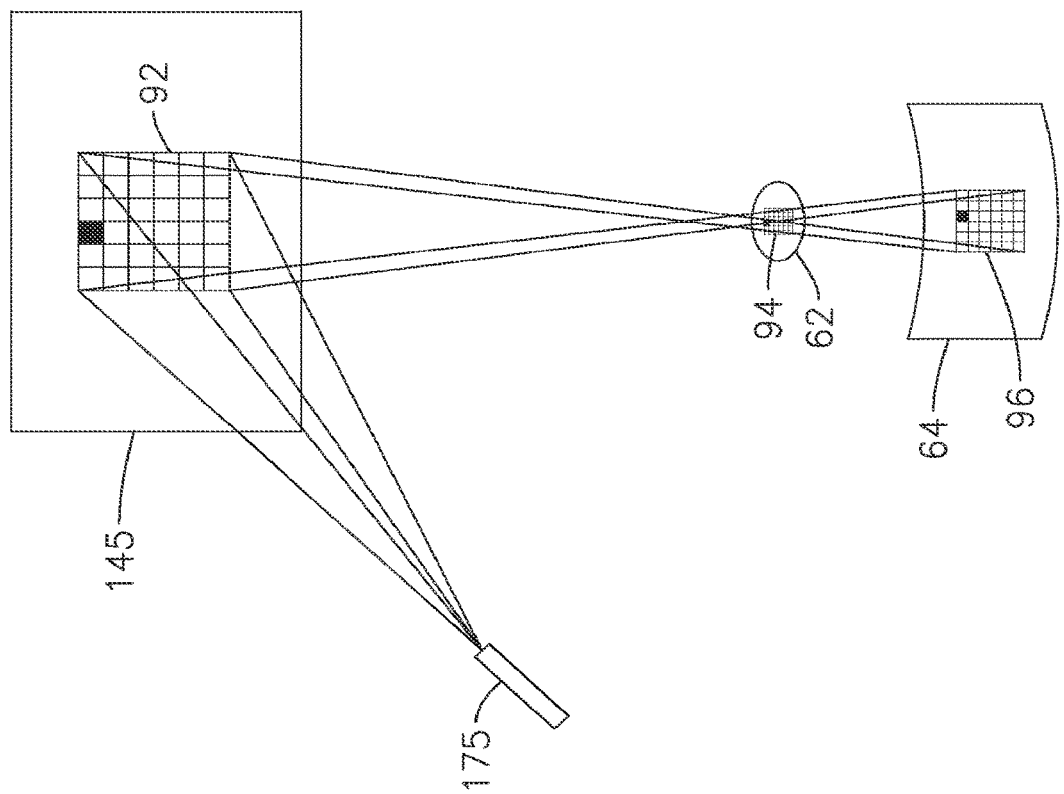

In one embodiment shown in FIG. 10, the light paths of multiple right light signals and multiple left light signals from light signal generators to retinas are illustrated. The multiple right light signals generated from the right light signal generator 170 are projected onto the right beam splitter 140 to form a right splitter image (RSI) 82. These multiple right light signals are redirected by the right beam splitter 140 and converge into a small right pupil image (RPI) 84 to pass through the right pupil 52, and then eventually arrive the right retina 54 to form a right retina image (RRI) 86. Each of the RSI, RPI, and RRI comprises i×j pixels. Each right light signal RLS(i,j) travels through the same corresponding pixels from RSI(i,j), to RPI(i,j), and then to RRI(x,y). For example RLS(5,3) travels from RSI (5,3), to RPI(5,3) and then to RRI(2,4). Likewise, the multiple left light signals generated from the left light signal generator 175 are projected onto the left beam splitter 145 to form a left splitter image (LSI) 92. These multiple left light signals are redirected by the left beam splitter 145 and converge into a small left pupil image (LPI) 94 to pass through the left pupil 62, and then eventually arrive the left retina 64 to form a right retina image (LRI) 96. Each of the LSI, LPI, and LRI comprises i×j pixels. Each left light signal LLS(i,j) travels through the same corresponding pixels from LCI(i,j), to LPI(i,j), and then to LRI(x,y). For example LLS(3,1) travels from LCI(3,1), to LPI(3,1) and then to LRI(4,6). The (0, 0) pixel is the top and left most pixel of each image. Pixels in the retina image is left-right inverted and top-bottom inverted to the corresponding pixels in the splitter image. Based on appropriate arrangements of the relative positions and angles of the light signal generators and beam splitters, each light signal has its own light path from a light signal generator to a retina. The combination of one right light signal displaying one right pixel on the right retina and one corresponding left light signal displaying one left pixel on the left retina forms a virtual binocular pixel with a specific depth perceived by a viewer. Thus, a virtual binocular pixel in the space can be represented by a pair of right retina pixel and left retina pixel or a pair of right splitter pixel and left splitter pixel.

A virtual image perceived by a viewer in area C includes multiple virtual binocular pixels. To precisely describe the location of a virtual binocular pixel in the space, each location in the space is provided a three dimensional (3D) coordinate, for example XYZ coordinate. Other 3D coordinate system can be used in another embodiment. As a result, each virtual binocular pixel has a 3D coordinate—a horizontal direction, a vertical direction, and a depth direction. A horizontal direction (or X axis direction) is along the direction of interpupillary line. A vertical direction (or Y axis direction) is along the facial midline and perpendicular to the horizontal direction. A depth direction (or Z axis direction) is normal to the frontal plane and perpendicular to both the horizontal and vertical directions. The horizontal direction coordinate and vertical direction coordinate are collectively referred to as the location in the present invention.

Figure 11:
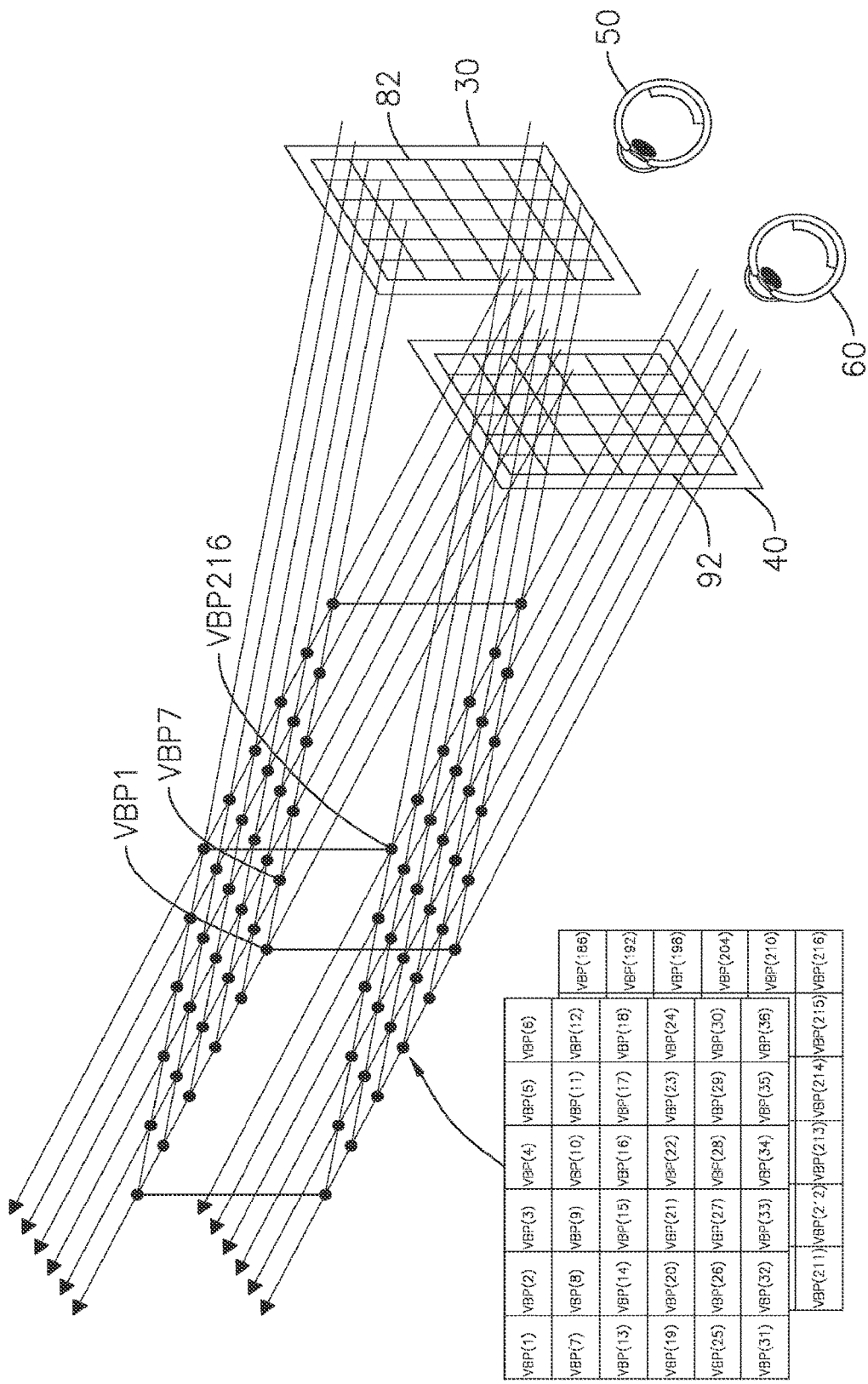
FIG. 11 is a schematic diagram illustrating the virtual binocular pixels formed by right light signals and left light signals in accordance with the present invention.

FIG. 11 illustrates the relationship between pixels in the right splitter image, pixels in the left splitter image, and the virtual binocular pixels. As described above, pixels in the right splitter image are one to one correspondence to pixels in the right retina image (right pixels). Pixels in the left splitter image are one to one correspondence to pixels in the left retina image (left pixels). However, pixels in the retina image is left-right inverted and top-bottom inverted to the corresponding pixels in the combiner image. However, if eyepieces 152, 154 are available in the system 100, the relationship between the pixels in the splitter image and the corresponding pixels in the retina image may be further modified by the optical features of the eyepieces. For a right retina image comprising 36 (6×6) right pixels and a left retina image comprising 36 (6×6) right pixels, there are 216 (6×6×6) virtual binocular pixels (shown as a dot) in the area C assuming all light signals are within FOV of both eyes of the viewer. The light path extension of one redirected right light signal intersects the light path extension of each redirected left light signal on the same row of the image. Likewise, the light path extension of one redirected left light signal intersects the light path extension of each redirected right light signal on the same row of the image. Thus, there are 36 (6×6) virtual binocular pixels on one layer and 6 layers in the space. There is usually a small angle between two adjacent lines representing light path extensions to intersect and form virtual binocular pixels although they are shown as parallel lines in the FIG. 11. A right pixel and a corresponding left pixel at approximately the same height of each retina (i.e. the same row of the right retina image and left retina image) tend to fuse earlier. As a result, right pixels are paired with left pixels at the same row of the retina image to form virtual binocular pixels.

As shown in FIG. 12, a look-up table is created to facilitate identifying the right pixel and left pixel pair for each virtual binocular pixel. For example, 216 virtual binocular pixels, numbering from 1 to 216, are formed by 36 (6×6) right pixels and 36 (6×6) left pixels. The first ($1^{st}$) virtual binocular pixel VBP(1) represents the pair of right pixel RRI(1,1) and left pixel LRI(1,1). The second ($2^{nd}$) virtual binocular pixel VBP(2) represents the pair of right pixel RRI(2,1) and left pixel LRI(1,1). The seventh ($7^{th}$) virtual binocular pixel VBP(7) represents the pair of right pixel RRI(1,1) and left pixel LRI(2,1). The thirty-seventh (37th) virtual binocular pixel VBP(37) represents the pair of right pixel RRI(1,2) and left pixel LRI(1,2). The two hundred and sixteenth ($216^{th}$) virtual binocular pixel VBP(216) represents the pair of right pixel RRI(6,6) and left pixel LRI(6,6). Thus, in order to display a specific virtual binocular pixel of a virtual image in the space for the viewer, it is determined which pair of the right pixel and left pixel can be used for generating the corresponding right light signal and left light signal. In addition, each row of a virtual binocular pixel on the look-up table includes a pointer which leads to a memory address that stores the perceived depth (z) of the VBP and the perceived position (x,y) of the VBP. Additional information, such as scale of size, number of overlapping objects, and depth in sequence depth etc., can also be stored for the VBP. Scale of size may be the relative size information of a specific VBP compared against a standard VBP. For example, the scale of size may be set to be 1 when the virtual image is displayed at a standard VBP that is 1 m in front of the viewer. As a result, the scale of size may be set to be 1.2 for a specific VBP that is 90 cm in front of the viewer. Likewise, when the scale of size may be set to be 0.8 for a specific VBP that is 1.5 m in front of the viewer. The scale of size can be used to determine the size of the virtual image for displaying when the virtual image is moved from a first depth to a second depth. Scale of size may be the magnification in the present invention. The number of overlapping objects is the number of objects that are overlapped with one another so that one object is completely or partially hidden behind another object. The depth in sequence provides information about sequence of depths of various overlapping images. For example, 3 images overlapping with each other. The depth in sequence of the first image in the front may be set to be 1 and the depth in sequence of the second image hidden behind the first image may be set to be 2. The number of overlapping images and the depth in sequence may be used to determine which and what portion of the images need to be displayed when various overlapping images are in moving.

The look up table may be created by the following processes. At the first step, obtain an individual virtual map based on his/her IPD, created by the virtual image module during initiation or calibration, which specify the boundary of the area C where the viewer can perceive a virtual image with depths because of the fusion of right retina image and left retina image. At the second step, for each depth at Z axis direction (each point at Z-coordinate), calculate the convergence angle to identify the pair of right pixel and left pixel respectively on the right retina image and the left retina image regardless of the X-coordinate and Y-coordinate location. At the third step, move the pair of right pixel and left pixel along X axis direction to identify the X-coordinate and Z-coordinate of each pair of right pixel and left pixel at a specific depth regardless of the Y-coordinate location. At the fourth step, move the pair of right pixel and left pixel along Y axis direction to determine the Y-coordinate of each pair of right pixel and left pixel. As a result, the 3D coordinate system such as XYZ of each pair of right pixel and left pixel respectively on the right retina image and the left retina image can be determined to create the look up table. In addition, the third step and the fourth step are exchangeable.

The light signal generator 170 and 175 may use laser, light emitting diode ("LED") including mini and micro LED, organic light emitting diode ("OLED"), or superluminescent diode ("SLD"), LCoS (Liquid Crystal on Silicon), liquid crystal display ("LCD"), or any combination thereof as its light source. In one embodiment, the light signal generator 170 and 175 is a laser beam scanning projector (LBS projector) which may comprise the light source including a red color light laser, a green color light laser, and a blue color light laser, a light color modifier, such as Dichroic combiner and Polarizing combiner, and a two dimensional (2D) adjustable reflector, such as a 2D electromechanical system ("MEMS") mirror. The 2D adjustable reflector can be replaced by two one dimensional (1D) reflector, such as two 1D MEMS mirror. The LBS projector sequentially generates and scans light signals one by one to form a 2D image at a predetermined resolution, for example 1280×720 pixels per frame. Thus, one light signal for one pixel is generated and projected at a time towards the beam splitter 140, 145. For a viewer to see such a 2D image from one eye, the LBS projector has to sequentially generate light signals for each pixel, for example 1280×720 light signals, within the time period of persistence of vision, for example $\frac{1}{18}$ second. Thus, the time duration of each light signal is about 60.28 nanosecond.

In another embodiment, the light signal generator 170 and 175 may be a digital light processing projector ("DLP projector") which can generate a 2D color image at one time. Texas Instrument's DLP technology is one of several technologies that can be used to manufacture the DLP projector. The whole 2D color image frame, which for example may comprise 1280×720 pixels, is simultaneously projected towards the splitters 140 and 145.

The beam splitter 140, 145 receives and redirects multiple light signals generated by the light signal generator 170, 175. In one embodiment, the beam splitter 140, 145 reflects the multiple light signals so that the redirected light signals are on the same side of the beam splitter 140, 145 as the incident light signals. In another embodiment, the beam splitter 140, 145 refracts the multiple light signals so that the redirected light signals are on the different side of the beam splitter 140, 145 from the incident light signals. When the beam splitter 140, 145 functions as a refractor. The reflection ratio can vary widely, such as 20%-80%, in part depending on the power of the light signal generator. People with ordinary skill in the art know how to determine the appropriate reflection ratio based on characteristics of the light signal generators and the splitters. Besides, in one embodiment, the beam splitter 140, 145 is optically transparent to the ambient (environmental) lights from the opposite side of the incident light signals so that the viewer can observe the real-time image at the same time. The degree of transparency can vary widely depending on the application. For AR/MR application, the transparency is preferred to be more than 50%, such as about 75% in one embodiment. In addition to redirecting the light signals, the focus adjustment unit 182, 187 may converge the multiple light signals so that they can pass through the pupils and arrive the retinas of the viewer's both eyes.

The beam splitter 140, 145 may be made of glasses or plastic materials like lens, coated with certain materials such as metals to make it partially transparent and partially reflective. One advantage of using a reflective splitter instead of a wave guide in the prior art for directing light signals to the viewer's eyes is to eliminate the problem of undesirable diffraction effects, such as multiple shadows, color displacement . . . etc.

The foregoing description of embodiments is provided to enable any person skilled in the art to make and use the subject matter. Various modifications to these embodiments will be readily apparent to those skilled in the art, and the novel principles and subject matter disclosed herein may be applied to other embodiments without the use of the innovative faculty. The claimed subject matter set forth in the claims is not intended to be limited to the embodiments shown herein but is to be accorded the widest scope consistent with the principles and novel features disclosed herein. It is contemplated that additional embodiments are within the spirit and true scope of the disclosed subject matter. Thus, it is intended that the present invention covers modifications and variations that come within the scope of the appended claims and their equivalents.

What is claimed is:

1. A virtual image module for generating a virtual image with depth, comprising:
a right light signal generator for generating a right light signal which is directed towards one retina of a viewer;
a left light signal generator for generating a left light signal corresponding to the right light signal which is directed towards the other retina of the viewer;
wherein the right light signal and the left light signal form a binocular pixel of a virtual image with a first depth, the first depth which the viewer perceives is modified by changing a convergence angle between light path extensions of the right light signal and the corresponding left light signal projected into the viewer's eyes based on an interpupillary distance,
wherein the virtual image is augmented and superimposed to a real-time image having a second depth and a magnification of the real-time image, the real-time image is generated by a real-time image module,
wherein the first depth and a magnification of the virtual image are altered according to the second depth,
wherein the virtual image module is inclusive in a portable augmented reality device which comprises the real-time image module.

2. The virtual image module for generating a virtual image with depth of claim 1, wherein the first depth and the magnification of the virtual image are altered according to the magnification of the real time image and the second depth, the portable augmented reality device is a portable augmented reality surgical microscope.

3. The virtual image module for generating a virtual image with depth of claim 1, wherein the second depth is perceived by the viewer to be approximately the same as the first depth perceived by the viewer.

4. The virtual image module for generating a virtual image with depth of claim 1, wherein the right light signal generator is located closely to a right portion of the real-time image module and the left light signal generator is located closely to a left portion of the real-time image module, the right light signal and the left light signal are respectively directed by a right beam splitter and a left beam splitter of the real-time image module towards the retinas of the viewer, an orientation of the right beam splitter and the left beam splitter can be changed.

5. The virtual image module for generating a virtual image with depth of claim 1, wherein the real-time image is generated by lights reflected or emitted from an object.

6. The virtual image module for generating a virtual image with depth of claim 1, wherein the virtual image is a photograph, a magnetic resonance image, an x-ray image, a computed tomography, and an optical coherence tomography of a body organ or tissue provided by the virtual image module.

7. The virtual image module for generating a virtual image with depth of claim 6, wherein the virtual image is marked with a location, a guidance, an instruction, or a navigation to perform a surgery.

8. The virtual image module for generating a virtual image with depth of claim 1, wherein a first point on the real-time image is selected as a first landmark for superimposing the virtual image on the real-time image by overlapping a corresponding first landmark on the virtual image on the first landmark on the real-time image.

9. The virtual image module for generating a virtual image with depth of claim 8, wherein a second point on the real-time image is selected as a second landmark for superimposing the virtual image on the real-time image by overlapping a corresponding second landmark on the virtual image on the second landmark on the real-time image.

10. The virtual image module for generating a virtual image with depth of claim 1, wherein the virtual image module further comprises a control module to process the right light signal and the corresponding left light signal so that the virtual image is modified to be superimposed on the real-time image based on a view angle, a location and the magnification of the real-time image.

11. The virtual image module for generating a virtual image with depth of claim 1, further comprising:
a user interface configured for the viewer to control a location and the first depth of the virtual image.

12. The virtual image module for generating a virtual image with depth of claim 1, further comprising:
an object measuring module configured to measure a location and a depth of the object.

13. The virtual image module for generating a virtual image with depth of claim 1, further comprising:
a recording module to record either the real-time image or the virtual image or both the real-time image and the virtual image.

14. The virtual image module for generating a virtual image with depth of claim 1, wherein the virtual image module further comprises a support structure wearable on a head of the viewer;
wherein the right light signal generator and the left light signal generator are carried by the support structure; and
wherein the right beam splitter and the left beam splitter are carried by the support structure and positioned within a field of view of the viewer.

* * * * *